United States Patent
Lubitz et al.

(10) Patent No.: US 6,596,510 B1
(45) Date of Patent: Jul. 22, 2003

(54) SECRETION OF CARRIER-BOUND PROTEINS INTO THE PERIPLASMA AND THE EXTRACELLULAR SPACE

(75) Inventors: Werner Lubitz, Schönborngasse 12/7, A-1080 Wien/Vienna (AT); Stephanie Resch, München (DE)

(73) Assignee: Werner Lubitz, Vienna (AT)

( * ) Notice: Subject to any disclaimer, the term of this patent is extended or adjusted under 35 U.S.C. 154(b) by 0 days.

(21) Appl. No.: 09/463,402

(22) PCT Filed: Jul. 27, 1998

(86) PCT No.: PCT/EP98/04723
§ 371 (c)(1),
(2), (4) Date: Mar. 30, 2000

(87) PCT Pub. No.: WO99/06567
PCT Pub. Date: Feb. 11, 1999

(30) Foreign Application Priority Data

Jul. 30, 1997 (DE) .......................... 197 32 829

(51) Int. Cl.[7] .......................... C12P 21/06; C12P 21/04; C12N 1/20; C12N 15/00; C07H 21/02; C07H 21/04

(52) U.S. Cl. .................. 435/69.1; 435/69.7; 435/252.3; 435/252.33; 435/320.1; 536/23.1; 536/23.5

(58) Field of Search ................ 435/69.1, 69.7, 435/320.1, 252.3, 252.33; 536/23.1, 23.5

(56) References Cited

FOREIGN PATENT DOCUMENTS

WO 95 19371 7/1995

OTHER PUBLICATIONS

Bingle et al. "Linker mutagenesis of the Caulobacter crescentus S–layer protein: . . . and a c–terminal secretion signal and the potential for heterologous protein secretion", J. of Bacteriology, 179 (3), pp. 601–611, Feb., 1997.*

Cover et al. "Supression of a signal sequence mutation by an amino acid substitution in the mature portion of the maltose binding protein", J. of Bacteroelogy, 169 (5), pp. 1794–1800, May, 1987.*

Cover et al. "*E. coli* mutant malE gene encoding periplasmic maltose–binding protein, 5' end." Database: GenEmbl, Accession No.: M16181, Apr. 26, 1993.*

Kuen et al., "Heterologous Expression and Self–Assembly of the S–Layer Protein SBSA of *Bacillus Stearothermophilus* in *Escherichia Coli*", MOLECULAR MICROBIOLOGY, vol. 19, No. 3, Feb. 1996, pp. 495–503.

Kuen et al., "Molecular characterization of the *Bacillus Stearothermophilus* PV72 S–Layer Gene SBSB Induced by Oxidative Stress", JOURNAL OF BACTERIOLOGY, vol. 179, No. 5, Mar. 1977, pp. 1664–1670.

Clement et al., "Secretion of a Bacterial Protein by Mammalian Cells", JOURNAL OF BIOTECHNOLOGY, vol. 43, No. 3, Dec. 15, 1995, pp. 169–181.

Peyret et al., "Characterization of the CSPB Gene Encoding PS2, An Ordered Surface–Layer Protein in Corynebacterium Glutamicum" MOLECULAR MICROBIOLOGY, vol. 9, No. 1, 1993, pp. 97–109.

* cited by examiner

Primary Examiner—Karen Cochrane Carlson
Assistant Examiner—Rita Mitra
(74) Attorney, Agent, or Firm—Rothwell, Figg, Ernst & Manbeck

(57) ABSTRACT

The present invention relates to processes for producing S-layer proteins and modified S-layer proteins in Gram-negative host cells.

12 Claims, 13 Drawing Sheets

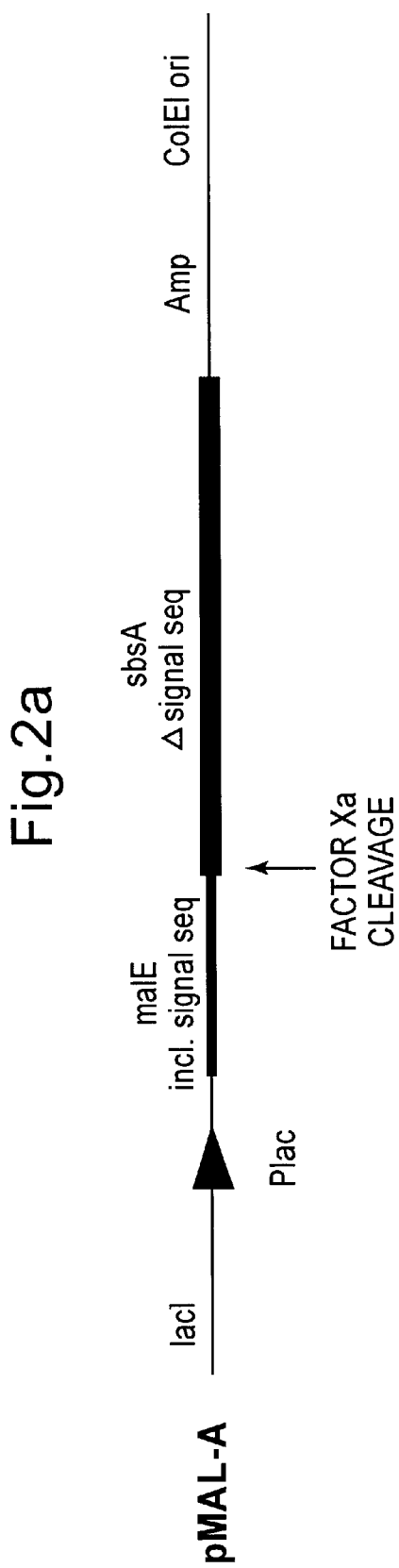

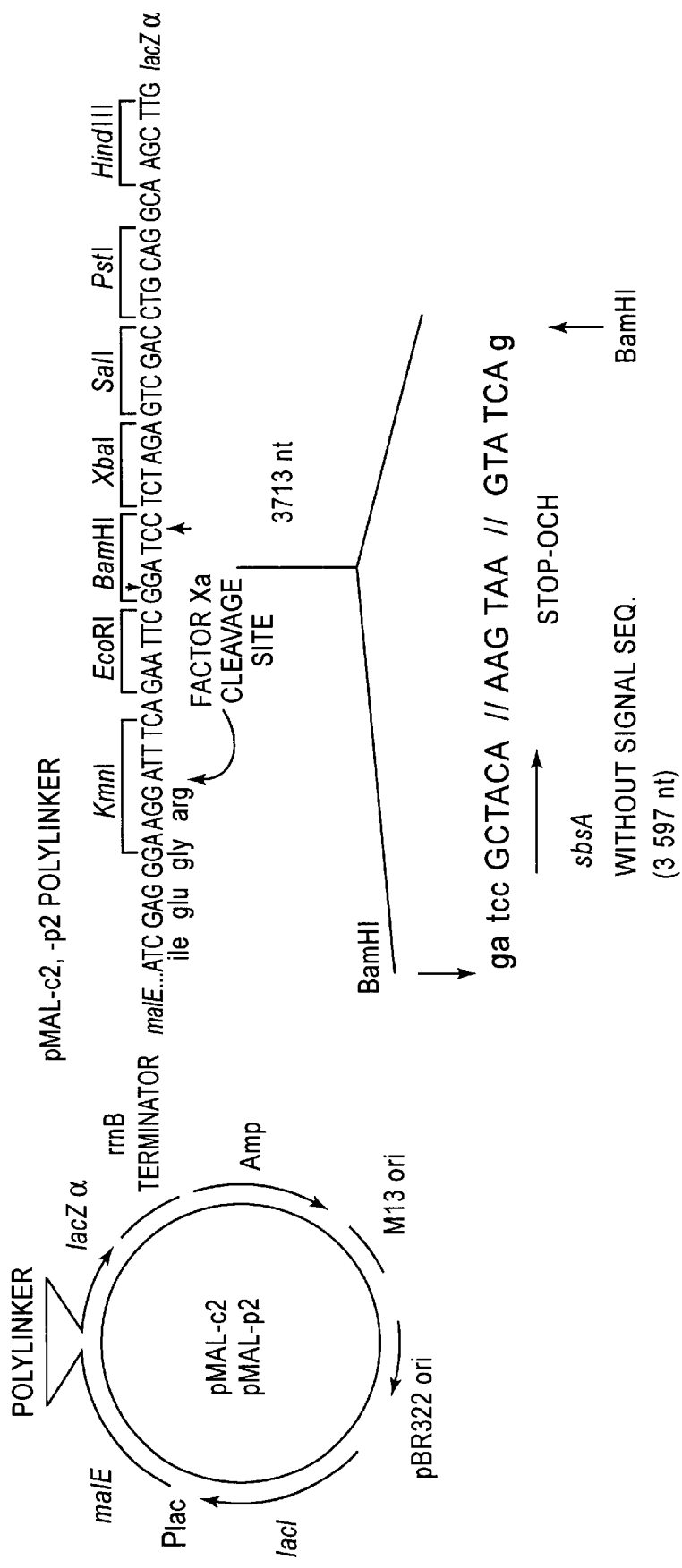

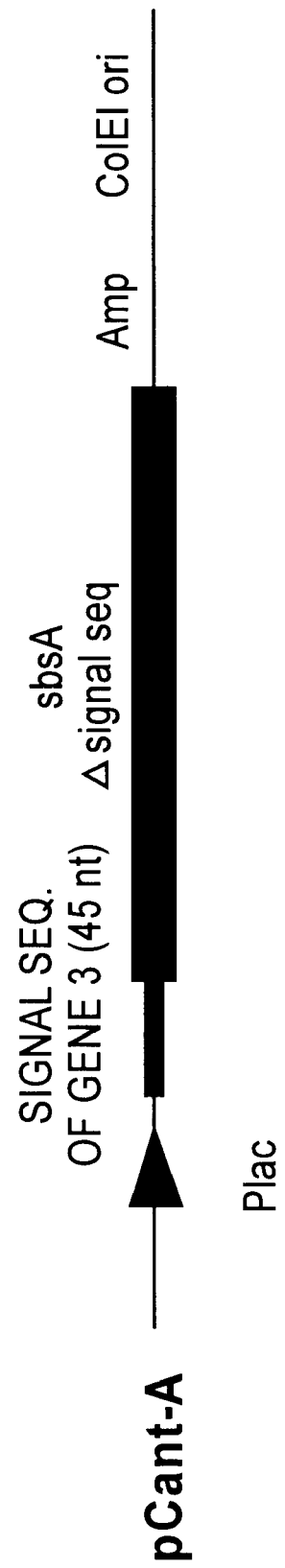

Fig.4a

Figure 1:
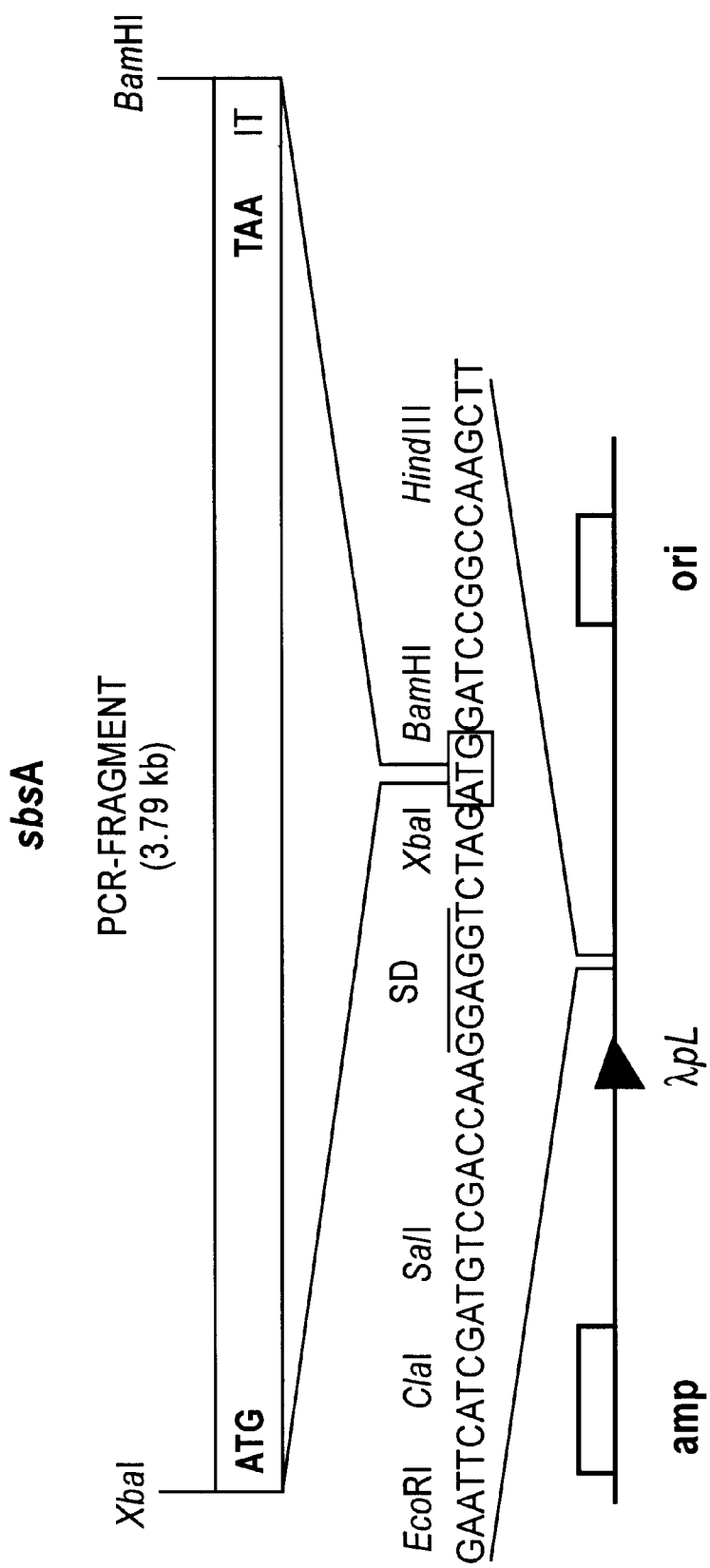

NUCLEOTIDE SEQUENCE OF AN SbsA GENE FUSED TO THE MALe
GENE INCLUDING ITS SIGNAL SEQUENCE (4988bp)
CLONING: MalE FROM pMal-p2 WITH SbsA (WITHOUT ss) IN
BamHI OF MCS
FEATURES:
POSITION 1249 TO 1254: BamHI CLEAVAGE SITE
POSITION 4956 TO 4961: BamHI CLEAVAGE SITE
POSITION 1255 TO 4851: SbsA GENE WITHOUT ITS OWN
　　　　　　　　　　　　SIGNAL SEQUENCE
*START OF MalE GENE WITH SIGNAL SEQUENCE*

```
ATGAAAATAA AAACAGGTGC ACGCATCCTC GCATTATCCG CATTAACGAC GATGATGTTT    60
TCCGCCTCGG CTCTCGCCAA AATCGAAGAA GGTAAACTGG TAATCTGGAT TAACGGCGAT   120
AAAGGCTATA ACGGTCTCGC TGAAGTCGGT AAGAAATTCG AGAAAGATAC CGGAATTAAA   180
GTCACCGTTG AGCATCCGGA TAAACTGGAA GAGAAATTCC CACAGGTTGC GGCAACTGGC   240
GATGGCCCTG ACATTATCTT CTGGGCACAC GACCGCTTTG GTGGCTACGC TCAATCTGGC   300
CTGTTGGCTG AAATCACCCC GGACAAAGCG TTCCAGGACA AGCTGTATCC GTTTACCTGG   360
GATGCCGTAC GTTACAACGG CAAGCTGATT GCTTACCCGA TCGCTGTTGA AGCGTTATCG   420
CTGATTTATA CAAAGATCT GCTGCCGAAC CCGCCAAAAA CCTGGGAAGA GATCCCGGCG   480
CTGGATAAAG AACTGAAAGC GAAAGGTAAG AGCGCGCTGA TGTTCAACCT GCAAGAACCG   540
TACTTCACCT GGCCGCTGAT TGCTGCTGAC GGGGGTTATG CGTTCAAGTA TGAAAACGGC   600
AAGTACGACA TTAAAGACGT GGGCGTGGAT AACGCTGGCG CGAAAGCGGG TCTGACCTTC   660
CTGGTTGACC TGATTAAAAA CAAACACATG AATGCAGACA CCGATTACTC CATCGCAGAA   720
GCTGCCTTTA ATAAAGGCGA ACAGCGATG ACCATCAACG GCCCGTGGGC ATGGTCCAAC   780
ATCGACACCA GCAAATTGAA TTATGGTGTA ACGGTACTGC CGACCTTCAA GGGTCACCCA   840
TCCAAACCGT TCGTTGGCGT GCTGAGCGCA GGTATTAACG CCGCCAGTCC GAACAAAGAG   900
TTGGCGAAAG AGTTCCTCGA AAACTATCTG CTGACTGATG AAGGTCTGGA AGCGGTTAAT   960
AAAGACAAAC CGCTGGGTGC CGTAGCGCTG AAGTCTTACG AGGAAGAGTT GGCGAAAGAT  1020
CCACGTATTG CCGCCACCAT GGAAAACGCC CAGAAAGGTG AAATCATGCC GAACATCCCG  1080
CAGATGTCCG CTTTCTGGTA TGCCGTGCGT ACTGCGGTGA TCAACGCCGC CAGCGGTCGT  1140
CAGATCGTCG ATGAAGCCCT GAAAGACGCG CAGACTAATT CGAGCTCGAA CAACAACAAC  1200
AATAACAATA ACAACAACCT CGGGATCGAG GGAAGGATTT CAGAATTCGG ATCCGCTACA  1260
```
　　　　　　　　　　　　　　　　　　　　　　　　*BamHI/START SbsA*
```
GATGTAGCAA CAGTAGTAAG CCAAGCAAAA GCACAGTTCA AAAAGCATA CTATACTTAC   1320
AGCCATACAG TAACGGAAAC TGGTGAATTC CCAAACATTA CGATGTATA TGCTGAATAC   1380
```

Fig.4b

```
AACAAAGCGA AAAAACGATA CCGTGATGCG GTAGCATTAG TGAATAAAGC AGGTGGCGCG    1440
AAAAAAGACG CTTACTTAGC TGATTTACAA AAAGAATATG AAACTTACGT TTTCAAAGCA    1500
AACCCTAAAT CTGGCGAAGC TCGTGTAGCA ACTTACATCG ATGCTTACAA CTATGCAACA    1560
AAATTAGACG AAATGCGCCA AGAGCTAGAG GCTGCTGTTC AAGCAAAAGA TTTAGAAAAA    1620
GCAGAACAAT ACTATCACAA AATTCCTTAT GAAATTAAAA CTCGCACAGT CATTTTAGAT    1680
CGCGTATATG GTAAAACAAC TCGTGATTTA CTTCGCTCTA CATTTAAAGC AAAAGCACAA    1740
GAACTTCGCG ACAGCTTAAT TTATGATATT ACCGTTGCAA TGAAAGCGCG CGAAGTACAA    1800
GACGCTGTGA AGCAGGCAA TTTAGACAAA GCTAAAGCTG CTGTTGATCA AATCAATCAA     1860
TACTTACCAA AAGTAACAGA TGCTTTCAAA ACTGAACTAA CAGAAGTAGC GAAAAAAGCA    1920
TTAGATGCAG ATGAAGCTGC GCTTACTCCA AAAGTTGAAA GTGTAAGTGC GATTAACACT    1980
CAAAACAAAG CTGTTGAATT AACAGCAGTA CCAGTGAACG GAACACTAAA ATTACAACTT    2040
TCAGCTGCTG CAAATGAAGA TACAGTAAAC GTAAATACTG TACGTATCTA TAAAGTGGAC    2100
GGTAACATTC CATTTGCCCT TAATACGGCA GATGTTTCTT TATCTACAGA CGGAAAAACT    2160
ATCACTGTGG ATGCTTCAAC TCCATTCGAA AATAATACGG AGTATAAAGT AGTAGTTAAA    2220
GGTATTAAAG ACAAAAATGG CAAAGAATTT AAAGAAGATG CATTCACTTT CAAGCTTCGA    2280
AATGATGCTG TAGTTACTCA AGTGTTTGGA ACTAATGTAA CAAACAACAC TTCTGTAAAC    2340
TTAGCAGCAG GTACTTTCGA CACTGACGAT ACTTTAACAG TAGTATTTGA TAAGTTGTTA    2400
GCACCTGAAA CTGTAAACAG CTCGAACGTT ACTATTACAG ATGTTGAAAC TGGAAAACGC    2460
ATTCCAGTAA TTGCATCTAC TTCTGGTTCT ACAATTACTA TTACGTTAAA AGAAGCGTTA    2520
GTAACTGGTA ACAATATAA ACTTGCTATC AATAATGTTA AAACATTAAC TGGTTACAAT     2580
GCAGAAGCTT ACGAGTTAGT GTTCACTGCA AACGCATCAG CACCAACTGT TGCTACCGCT    2640
CCTACTACTT TAGGTGGTAC AACTTTATCT ACTGGTTCTC TTACAACAAA TGTTTGGGGT    2700
AAATTGGCTG GTGGTGTGAA TGAAGCTGGA ACTTATTATC CTGGTCTTCA ATTCACAACA    2760
ACGTTTGCTA CTAAGTTAGA CGAATCTACT TTAGCTGATA ACTTTGTATT AGTTGAAAAA    2820
GAATCTGGTA CAGTTGTTGC TTCTGAACTA AAATATAATG CAGACGCTAA AATGGTAACT    2880
TTAGTGCCAA AAGCGGACCT TAAAGAAAAT ACAATCTATC AAATCAAAAT TAAAAAAGGC    2940
TTGAAGTCCG ATAAAGGTAT TGAATTAGGC ACTGTTAACG AGAAAACATA TGAGTTCAAA    3000
ACTCAAGACT TAACTGCTCC TACAGTTATT AGCGTAACGT CTAAAAATGG CGACGCTGGA    3060
TTAAAAGTAA CTGAAGCTCA AGAATTTACT GTGAAGTTCT CAGAGAATTT AAATACATTT    3120
AATGCTACAA CCGTTTCGGG TAGCACAATC ACATACGGTC AAGTTGCTGT AGTAAAAGCG    3180
```

Fig.4c

```
GGTGCAAACT TATCTGCTCT TACAGCAAGT GACATCATTC CAGCTAGTGT TGAAGCGGTT   3240
ACTGGTCAAG ATGGAACATA CAAAGTGAAA GTTGCTGCTA ACCAATTAGA ACGTAACCAA   3300
GGGTACAAAT TAGTAGTGTT CGGTAAAGGT GCAACAGCTC CTGTTAAAGA TGCTGCAAAT   3360
GCAAATACTT TAGCAACTAA CTATATCTAT ACATTACAA CTGAAGGTCA AGACGTAACA    3420
GCACCAACGG TTACAAAAGT ATTCAAAGGT GATTCTTTAA AAGACGCTGA TGCAGTTACT   3480
ACACTTACGA ACGTTGATGC AGGTCAAAAA TTCACTATCC AATTTAGCGA AGAATTAAAA   3540
ACTTCTAGTG GTTCTTTAGT GGGTGGCAAA GTAACTGTCG AGAAATTAAC AAACAACGGA   3600
TGGGTAGATG CTGGTACTGG AACAACTGTA TCAGTTGCTC CTAAGACAGA TGCAAATGGT   3660
AAAGTAACAG CTGCTGTGGT TACATTAACT GGTCTTGACA ATAACGACAA AGATGCGAAA   3720
TTGCGTCTGG TAGTAGATAA GTCTTCTACT GATGGAATTG CTGATGTAGC TGGTAATGTA   3780
ATTAAGGAAA AAGATATTTT AATTCGTTAC AACAGCTGGA GACACACTGT AGCTTCTGTG   3840
AAAGCTGCTG CTGACAAAGA TGGTCAAAAC GCTTCTGCTG CATTCCCAAC AAGCACTGCA   3900
ATTGATACAA CTAAGAGCTT ATTAGTTGAA TTCAATGAAA CTGATTTAGC GGAAGTTAAA   3960
CCTGAGAACA TCGTTGTTAA AGATGCAGCA GGTAATGCGG TAGCTGGTAC TGTAACAGCA   4020
TTAGACGGTT CTACAAATAA ATTTGTATTC ACTCCATCTC AAGAATTAAA AGCTGGTACA   4080
GTTTACTCTG TAACAATTGA CGGTGTGAGA GATAAAGTAG GTAACACAAT CTCTAAATAC   4140
ATTACTTCGT TCAAGACTGT ATCTGCGAAT CCAACGTTAT CTTCAATCAG CATTGCTGAC   4200
GGTGCAGTTA ACGTTGACCG TTCTAAAACA ATTACAATTG AATTCAGCGA TTCAGTTCCA   4260
AACCCAACAA TCACTCTTAA GAAGGCTGAC GGAACTTCAT TTACTAATTA CACTTTAGTA   4320
AATGTAAATA ATGAAAATAA AACATACAAA ATTGTATTCC ACAAAGGTGT AACACTTGAC   4380
GAGTTTACTC AATATGAGTT AGCAGTTTCA AAAGATTTTC AAACTGGTAC TGATATTGAT   4440
AGCAAAGTTA CATTCATCAC AGGTTCTGTT GCTACTGACG AAGTAAAACC TGCTCTAGTA   4500
GGCGTTGGTT CATGGAATGG AACAAGCTAT ACTCAGGATG CTGCAGCAAC ACGACTTCGG   4560
TCTGTAGCTG ACTTCGTTGC GGAGCCAGTT GCCCTTCAAT TCTCAGAAGG TATCGATTTA   4620
ACGAATGCAA CTGTGACAGT AACAAATATT ACTGATGATA AAACTGTTGA AGTTATTTCA   4680
AAAGAGAGTG TAGACGCAGA CCATGATGCA GGTGCTACTA AGGAGACATT AGTAATTAAC   4740
ACAGTTACTC CTTTAGTACT TGATAACAGC AAGACTTATA AGATTGTTGT AAGTGGAGTT   4800
                                                    STOP SbsA
AAAGATGCAG CAGGTAATGT TGCAGATACT ATTACATTCT ATATTAAGTA ATCTGGGCTA   4860
GGTGTTTGTC ACCGCTCAAG GTTGTCAAAA TATGTCGAAA AGCTCTGCGG AGAGAAATCT   4920
                                                BamHI
CTGCGGGGCT TTTCTTTTTG CTCAAATCTG TATCAGGATC CTCTAGAGTC GACCTGCAGG   4980
CAAGCTTG                                                            4988
```

Fig.5a

NUCLEOTIDE SEQUENCE OF AN SbsA GENE FUSED TO THE SIGNAL
SEQUENCE OF GENE 3 OF BACTERIOPHAGE fd (3768bp)
CLONING: SbsA (WITHOUT ss) SfiI-NotI) IN pCANTAB5E
(SfiI-NotI)

FEATURES:
POSITION 48 TO 60:      SfiI CLEAVAGE SITE
POSITION 3761 TO 3768:  NotI CLEAVAGE SITE
POSITION 61 TO 3657:    SbsA GENE WITHOUT ITS OWN
                        SIGNAL SEQUENCE

```
    SIGNAL SEQUENCE                                        SfiI
GTGAAAAAAT TATTATTCGC AATTCCTTTA GTTGTTCCTT TCTATGCGGC CCAGCCGGCC    60
START OF SbsA WITHOUT SIGNAL SEQUENCE
GCTACAGATG TAGCAACAGT AGTAAGCCAA GCAAAAGCAC AGTTCAAAAA AGCATACTAT   120
ACTTACAGCC ATACAGTAAC GGAAACTGGT GAATTCCCAA ACATTAACGA TGTATATGCT   180
GAATACAACA AAGCGAAAAA ACGATACCGT GATGCGGTAG CATTAGTGAA TAAAGCAGGT   240
GGCGCGAAAA AAGACGCTTA CTTAGCTGAT TTACAAAAAG AATATGAAAC TTACGTTTTC   300
AAAGCAAACC CTAAATCTGG CGAAGCTCGT GTAGCAACTT ACATCGATGC TTACAACTAT   360
GCAACAAAAT TAGACGAAAT GCGCCAAGAG CTAGAGGCTG CTGTTCAAGC AAAAGATTTA   420
GAAAAAGCAG AACAATACTA TCACAAAATT CCTTATGAAA TTAAAACTCG CACAGTCATT   480
TTAGATCGCG TATATGGTAA ACAACTCGT GATTTACTTC GCTCTACATT TAAAGCAAAA    540
GCACAAGAAC TTCGCGACAG CTTAATTTAT GATATTACCG TTGCAATGAA AGCGCGCGAA   600
GTACAAGACG CTGTGAAAGC AGGCAATTTA GACAAAGCTA AGCTGCTGT TGATCAAATC    660
AATCAATACT TACCAAAAGT AACAGATGCT TTCAAAACTG AACTAACAGA AGTAGCGAAA   720
AAAGCATTAG ATGCAGATGA AGCTGCGCTT ACTCCAAAAG TTGAAAGTGT AAGTGCGATT   780
AACACTCAAA ACAAAGCTGT TGAATTAACA GCAGTACCAG TGAACGGAAC ACTAAAATTA   840
CAACTTTCAG CTGCTGCAAA TGAAGATACA GTAAACGTAA ATACTGTACG TATCTATAAA   900
GTGGACGGTA ACATTCCATT TGCCCTTAAT ACGGCAGATG TTTCTTTATC TACAGACGGA   960
AAAACTATCA CTGTGGATGC TTCAACTCCA TTCGAAAATA TACGGAGTA TAAAGTAGTA   1020
GTTAAAGGTA TTAAAGACAA AAATGGCAAA GAATTTAAAG AAGATGCATT CACTTTCAAG  1080
CTTCGAAATG ATGCTGTAGT TACTCAAGTG TTTGGAACTA ATGTAACAAA CAACACTTCT  1140
GTAAACTTAG CAGCAGGTAC TTTCGACACT GACGATACTT TAACAGTAGT ATTTGATAAG  1200
TTGTTAGCAC CTGAAACTGT AAACAGCTCG AACGTTACTA TTACAGATGT TGAAACTGGA  1260
AAACGCATTC AGTAATTGC ATCTACTTCT GGTTCTACAA TTACTATTAC GTTAAAAGAA   1320
GCGTTAGTAA CTGGTAAACA ATATAAACTT GCTATCAATA ATGTTAAAAC ATTAACTGGT  1380
TACAATGCAG AAGCTTACGA GTTAGTGTTC ACTGCAAACG CATCAGCACC AACTGTTGCT  1440
ACCGCTCCTA CTACTTTAGG TGGTACAACT TTATCTACTG GTTCTCTTAC AACAAATGTT  1500
```

Fig.5b

```
TGGGGTAAAT TGGCTGGTGG TGTGAATGAA GCTGGAACTT ATTATCCTGG TCTTCAATTC  1560
ACAACAACGT TTGCTACTAA GTTAGACGAA TCTACTTTAG CTGATAACTT TGTATTAGTT  1620
GAAAAAGAAT CTGGTACAGT TGTTGCTTCT GAACTAAAAT ATAATGCAGA CGCTAAAATG  1680
GTAACTTTAG TGCCAAAAGC GGACCTTAAA GAAAATACAA TCTATCAAAT CAAAATTAAA  1740
AAAGGCTTGA AGTCCGATAA AGGTATTGAA TTAGGCACTG TTAACGAGAA AACATATGAG  1800
TTCAAAACTC AAGACTTAAC TGCTCCTACA GTTATTAGCG TAACGTCTAA AAATGGCGAC  1860
GCTGGATTAA AAGTAACTGA AGCTCAAGAA TTTACTGTGA AGTTCTCAGA GAATTTAAAT  1920
ACATTTAATG CTACAACCGT TTCGGGTAGC ACAATCACAT ACGGTCAAGT TGCTGTAGTA  1980
AAAGCGGGTG CAAACTTATC TGCTCTTACA GCAAGTGACA TCATTCCAGC TAGTGTTGAA  2040
GCGGTTACTG GTCAAGATGG AACATACAAA GTGAAAGTTG CTGCTAACCA ATTAGAACGT  2100
AACCAAGGGT ACAAATTAGT AGTGTTCGGT AAAGGTGCAA CAGCTCCTGT TAAAGATGCT  2160
GCAAATGCAA ATACTTTAGC AACTAACTAT ATCTATACAT TTACAACTGA AGGTCAAGAC  2220
GTAACAGCAC CAACGGTTAC AAAAGTATTC AAAGGTGATT CTTTAAAAGA CGCTGATGCA  2280
GTTACTACAC TTACGAACGT TGATGCAGGT CAAAAATTCA CTATCCAATT TAGCGAAGAA  2340
TTAAAAACTT CTAGTGGTTC TTTAGTGGGT GGCAAAGTAA CTGTCGAGAA ATTAACAAAC  2400
AACGGATGGG TAGATGCTGG TACTGGAACA ACTGTATCAG TTGCTCCTAA GACAGATGCA  2460
AATGGTAAAG TAACAGCTGC TGTGGTTACA TTAACTGGTC TTGACAATAA CGACAAAGAT  2520
GCGAAATTGC GTCTGGTAGT AGATAAGTCT TCTACTGATG GAATTGCTGA TGTAGCTGGT  2580
AATGTAATTA AGGAAAAAGA TATTTTAATT CGTTACAACA GCTGGAGACA CACTGTAGCT  2640
TCTGTGAAAG CTGCTGCTGA CAAAGATGGT CAAAACGCTT CTGCTGCATT CCCAACAAGC  2700
ACTGCAATTG ATACAACTAA GAGCTTATTA GTTGAATTCA ATGAAACTGA TTTAGCGGAA  2760
GTTAAACCTG AGAACATCGT TGTTAAAGAT GCAGCAGGTA ATGCGGTAGC TGGTACTGTA  2820
ACAGCATTAG ACGGTTCTAC AAATAAATTT GTATTCACTC CATCTCAAGA ATTAAAAGCT  2880
GGTACAGTTT ACTCTGTAAC AATTGACGGT GTGAGAGATA AGTAGGTAA CACAATCTCT  2940
AAATACATTA CTTCGTTCAA GACTGTATCT GCGAATCCAA CGTTATCTTC AATCAGCATT  3000
GCTGACGGTG CAGTTAACGT TGACCGTTCT AAAACAATTA CAATTGAATT CAGCGATTCA  3060
GTTCCAAACC CAACAATCAC TCTTAAGAAG CTGACGGAA CTTCATTTAC TAATTACACT  3120
TTAGTAAATG TAAATAATGA AAATAAAACA TACAAAATTG TATTCCACAA AGGTGTAACA  3180
CTTGACGAGT TTACTCAATA TGAGTTAGCA GTTTCAAAAG ATTTTCAAAC TGGTACTGAT  3240
ATTGATAGCA AAGTTACATT CATCACAGGT TCTGTTGCTA CTGACGAAGT AAAACCTGCT  3300
```

Fig.5c

```
CTAGTAGGCG TTGGTTCATG GAATGGAACA AGCTATACTC AGGATGCTGC AGCAACACGA  3360
CTTCGGTCTG TAGCTGACTT CGTTGCGGAG CCAGTTGCCC TTCAATTCTC AGAAGGTATC  3420
GATTTAACGA ATGCAACTGT GACAGTAACA AATATTACTG ATGATAAAAC TGTTGAAGTT  3480
ATTTCAAAAG AGAGTGTAGA CGCAGACCAT GATGCAGGTG CTACTAAGGA GACATTAGTA  3540
ATTAACACAG TTACTCCTTT AGTACTTGAT AACAGCAAGA CTTATAAGAT TGTTGTAAGT  3600
                                                    STOP SbsA
GGAGTTAAAG ATGCAGCAGG TAATGTTGCA GATACTATTA CATTCTATAT TAAGTAATCT  3660
GGGCTAGGTG TTTGTCACCG CTCAAGGTTG TCAAAATATG TCGAAAAGCT CTGCGGAGAG  3720
                                                 Not I
AAATCTCTGC GGGCTTTTC TTTTTGCTCA AATCTGTATC GCGGCCGC            3768
```

Fig.6a

NUCLEOTIDE SEQUENCE OF AN SbsB GENE FUSED TO THE MalE
GENE INCLUDING ITS SIGNAL SEQUENCE (4065bp)
CLONING: MalE FROM pMal-p2 WITH SbsB (WITHOUT ss) IN
BamHI OF MCS
FEATURES:
POSITION 1249 TO 1254: BamHI CLEAVAGE SITE
POSITION 4033 TO 4038: BamHI CLEAVAGE SITE
POSITION 1255 TO 3924: SbsB GENE WITHOUT ITS OWN
SIGNAL SEQUENCE

*START OF MalE GENE WITH SIGNAL SEQUENCE*

```
ATGAAAATAA AAACAGGTGC ACGCATCCTC GCATTATCCG CATTAACGAC GATGATGTTT    60
TCCGCCTCGG CTCTCGCCAA AATCGAAGAA GGTAAACTGG TAATCTGGAT TAACGGCGAT   120
AAAGGCTATA ACGGTCTCGC TGAAGTCGGT AAGAAATTCG AGAAAGATAC CGGAATTAAA   180
GTCACCGTTG AGCATCCGGA TAAACTGGAA GAGAAATTCC CACAGGTTGC GGCAACTGGC   240
GATGGCCCTG ACATTATCTT CTGGGCACAC GACCGCTTTG GTGGCTACGC TCAATCTGGC   300
CTGTTGGCTG AAATCACCCC GGACAAAGCG TTCCAGGACA AGCTGTATCC GTTTACCTGG   360
GATGCCGTAC GTTACAACGG CAAGCTGATT GCTTACCCGA TCGCTGTTGA AGCGTTATCG   420
CTGATTTATA ACAAAGATCT GCTGCCGAAC CCGCCAAAAA CCTGGGAAGA GATCCCGGCG   480
CTGGATAAAG AACTGAAAGC GAAAGGTAAG AGCGCGCTGA TGTTCAACCT GCAAGAACCG   540
TACTTCACCT GGCCGCTGAT TGCTGCTGAC GGGGGTTATG CGTTCAAGTA TGAAAACGGC   600
AAGTACGACA TTAAAGACGT GGGCGTGGAT AACGCTGGCG CGAAAGCGGG TCTGACCTTC   660
CTGGTTGACC TGATTAAAAA CAAACACATG AATGCAGACA CCGATTACTC CATCGCAGAA   720
GCTGCCTTTA ATAAAGGCGA AACAGCGATG ACCATCAACG GCCCGTGGGC ATGGTCCAAC   780
ATCGACACCA GCAAATTGAA TTATGGTGTA ACGGTACTGC CGACCTTCAA GGGTCACCCA   840
TCCAAACCGT TCGTTGGCGT GCTGAGCGCA GGTATTAACG CCGCCAGTCC GAACAAAGAG   900
TTGGCGAAAG AGTTCCTCGA AAACTATCTG CTGACTGATG AAGGTCTGGA AGCGGTTAAT   960
AAAGACAAAC CGCTGGGTGC CGTAGCGCTG AAGTCTTACG AGGAAGAGTT GGCGAAAGAT  1020
CCACGTATTG CCGCCACCAT GGAAAACGCC CAGAAAGGTG AAATCATGCC GAACATCCCG  1080
CAGATGTCCG CTTTCTGGTA TGCCGTGCGT ACTGCGGTGA TCAACGCCGC CAGCGGTCGT  1140
CAGATCGTCG ATGAAGCCCT GAAAGACGCG CAGACTAATT CGAGCTCGAA CAACAACAAC  1200
                                             BamHI / START SbsB
AATAACAATA ACAACAACCT CGGGATCGAG GGAAGGATTT CAGAATTCGG ATCCGCAAGC  1260
TTCACAGATG TTGCGCCGCA ATATAAAGAT GCGATCGATT TCTTAGTATC AACTGGTGCA  1320
ACAAAAGGTA AACAGAAAC AAAATTCGGC GTTTACGATG AAATCACTCG TCTAGATGCG  1380
GCAGTTATTC TTGCAAGAGT ATTAAAACTA GACGTTGACA ACGCAAAAGA CGCAGGCTTC  1440
ACAGATGTGC CAAAGACCG TGCAAAATAC GTCAACGCGC TTGTAGAAGC TGGCGTATTA  1500
```

Fig.6b

```
AACGGTAAAG CACCTGGCAA ATTTGGTGCA TACGACCCAT TAACTCGCGT TGAAAE-eTGGCA 1560
AAAATCATCG CGAACCGTTA CAAATTAAAA GCTGACGATG TAAAACTTCC ATTCACTGAT 1620
GTAAACGATA CATGGGCACC ATACGTAAAA GCGCTTTATA AATACGAAGT AACAAAAGGT 1680
AAAACACCAA CAAGCTTCGG TGCATACCAA AACATCACTC GCGGTGACTT TGCGCAATTT 1740
GTATATAGAG CGGTGAATAT TAATGCAGTG CCAGAAATAG TTGAAGTAAC TGCGGTTAAT 1800
TCGACTACAG TGAAAGTAAC ATTCAATACG CAAATTGCTG ATGTTGATTT CACAAATTTT 1860
GCTATCGATA ACGGTTTAAC TGTTACTAAA GCAACTCTTT CTCGTGATAA AAAATCCGTA 1920
GAGGTTGTGG TAAATAAACC GTTTACTCGT AATCAGGAAT ATACAATTAC AGCGACAGGC 1980
ATTAAAAATT TAAAAGGCGA GACCGCTAAG GAATTAACTG GTAAGTTTGT TTGGTCTGTT 2040
CAAGATGCGG TAACTGTTGC ACTAAATAAT AGTTCGCTTA AGTTGGAGA GGAATCTGGT 2100
TTAACTGTAA AAGATCAGGA TGGCAAAGAT GTTGTAGGTG CTAAAGTAGA ACTTACTTCT 2160
TCTAATACTA ATATTGTTGT AGTTTCAAGT GGCGAAGTAT CAGTATCTGC TGCTAAAGTT 2220
ACAGCTGTAA AACCGGGAAC AGCTGATGTT ACTGCAAAAG TTACATTACC AGATGGTGTT 2280
GTACTAACAA ATACATTTAA AGTGACAGTT ACAGAAGTGC CTGTGCAAGT ACAAAATCAA 2340
GGATTTACTT TAGTTGATAA TCTTTCTAAT GCTCCACAGA ATACAGTTGC ATTTAACAAA 2400
GCTGAGAAAG TAACTTCAAT GTTTGCTGGA GAAACTAAAA CAGTTGCAAT GTATGATACT 2460
AAAAACGGTG ATCCTGAAAC TAAACCTGTT GATTTCAAAG ATGCAACTGT ACGTTCATTA 2520
AATCCAATTA TTGCAACAGC TGCTATTAAT GGTAGTGAGC TCCTTGTCAC AGCTAATGCT 2580
GGCCAATCTG GAAAAGCTTC ATTTGAAGTA ACATTTAAAG ATAATACAAA AGAACATTT 2640
ACAGTTGATG TGAAAAAAGA CCCTGTATTA CAAGATATTA AGTAGATGC AACTTCTGTT 2700
AAACTTTCCG ATGAAGCTGT TGGCGGCGGG GAAGTTGAAG GAGTTAACCA AAAAACGATT 2760
AAAGTAAGTG CAGTTGACCA ATACGGTAAA GAAATTAAAT TTGGTACAAA AGGTAAAGTT 2820
ACTGTTACAA CTAATACAGA AGGACTAGTT ATTAAAAATG TAAATAGCGA TAATACAATT 2880
GACTTTGATA GCGGCAATAG TGCAACTGAC CAATTTGTTG TCGTTGCAAC AAAAGACAAA 2940
ATTGTCAATG GTAAAGTAGA AGTTAAATAT TTCAAAAATG CTAGTGACAC AACACCAACT 3000
TCAACTAAAA CAATTACTGT TAATGTAGTG AATGTAAAAG CTGACGCTAC ACCAGTAGGA 3060
TTAGATATTG TAGCACCTTC TGAAATTGAT GTGAATGCTC CAAACACTGC TTCTACTGCA 3120
GATGTTGATT TTATTAATTT CGAAAGTGTT GAGATTTATA CACTCGATTC TAATGGTAAC 3180
CGTCTTAAAA AAGTTACTCC AACTGCAACT ACACTTGTAG GTACTAATGA TTATGTTGAA 3240
GTTAATGGGA ATGTATTACA ATTCAAGGGT AACGATGAAT TAACGCTATT AACTTCTTCT 3300
```

Fig.6c

```
AGTACAGTAA ACGTTGATGT AACAGCTGAT GGAATTACAA AACGTATTCC AGTAAAATAT   3360
ATCAACTCTG CAAGTGTACC TGCCAGTGCA ACAGTAGCAA CAAGTCCTGT TACTGTTAAG   3420
CTTAATTCAA GTGATAATGA TTTAACATTT GAAGAATTAA TATTCGGTGT AATTGACCCT   3480
ACACAATTAG TCAAAGATGA AGACATCAAC GAATTTATTG CAGTTTCAAA AGCGGCTAAA   3540
AATGATGGAT ATTTGTATAA TAAACCGCTT GTAACGGTTA AAGATGCATC AGGAAAAGTT   3600
ATTCCAACAG GTGCAAATGT TTACGGTCTA AATCATGATG CAACTAACGG AAACATTTGG   3660
TTTGATGAGG AACAAGCTGG CTTAGCTAAA AAATTTAGTG ATGTACATTT TGATGTTGAT   3720
TTTTCATTAG CTAACGTTGT AAAAACTGGT AGCGGTACAG TTTCTTCATC GCCATCATTA   3780
TCTGACGCAA TTCAACTTAC TAATTCAGGC GATGCAGTAT CGTTTACATT AGTTATCAAA   3840
TCAATTTATG TTAAAGGCGC AGATAAAGAT GATAATAACT TACTTGCAGC CCCTGTTTCT   3900
           STOP SbsB
GTCAATGTGA CTGTGACAAA ATAATTTGA GGTTCGGTCT CTGTTACCAT TTGAAAAATG    3960
CCGAAAAGCT CTGCGGAGAG AAATCTCTGC GGGGCTTTTC TTTTTGGTTC TATGTCAATT   4020
       BamHI
GTTGAGGTGC ATGGATCCTC TAGAGTCGAC CTGCAGGCAA GCTTG                   4065
```

SECRETION OF CARRIER-BOUND PROTEINS INTO THE PERIPLASMA AND THE EXTRACELLULAR SPACE

This Application is a 371 of PCT/EP98/04723 filed on Jul. 27, 1998, which claims benefit of German Application 197 32 829.6 filed on Jul. 30, 1997.

The present invention relates to processes for producing carrier-bound proteins, in particular S-layer proteins and modified S-layer proteins in pro- or eukaryotic host cells.

Crystalline bacterial cell surface layers (S-layers) form in many eubacteria and in most archaebacteria of the outermost cell wall component (Sleytr et al. (1988), Crystalline Bacterial Cell Surface Layers, Springer Verlag Berlin; Messner and Sleytr. Adv. Mikrob. Physiol. 33 (1992), 213–275). Most of the S-layer proteins known at present are composed of identical proteins or glycoproteins which have apparent molecular weights in the range from 40,000 to 220,000. The components of S-layers are self-assembling and most lattices have oblique (p2), square (p4) or hexagonal (p6) symmetry. The functions of bacterial S-layers are still not completely known but, on the basis of their localization on the cell surface, it is likely that the porous crystalline S-layers act mainly as protective coverings, molecular sieves or for promoting cell adhesion and surface recognition.

Genetic data and sequence information are known for various S-layer genes from microorganisms. A review is to be found in Peyret et al., Mol. Microbiol. 9 (1993), 97–109. Express reference is made to these data. The sequence of the gene sbsA coding for the S-layer protein of B.stearothermophilus PV72 and a method for cloning it are indicated by Kuen et al. (Gene 145 (1994), 115–20). B.stearothermophilus PV72 is a Gram-positive bacterium which is covered by a hexagonally arranged S-layer. The main component of the S-layer is a 128 kd protein which is the commonest protein in the cell, comprising approximately 15% of the total protein constituents. Various strains of B.stearothermophilus have been characterized and differ in the type of, S-layer lattice, the molecular weight and the glycosylation of the S-layer components (Messner and Sleytr (1992), supra).

German Patent Application DE-A 44 25 527 discloses the signal peptide-encoding section of the S-layer gene of B.stearothermophilus and the amino acid sequence derived therefrom. The cleavage site between the signal peptide and the mature protein is located between position 30 and 31 of the amino acid sequence. The signal peptide-encoding nucleic acid can be operatively linked to a protein-encoding nucleic acid and used for the recombinant production of proteins in a process in which a transformed host cell is prepared, the host cell is cultivated under conditions which lead to expression of the nucleic acid and to production and secretion of the polypeptide encoded thereby, and the resulting polypeptide is isolated from the culture medium. The host cells mentioned as preferred are prokaryotic organisms, in particular Gram-positive organisms of the genus Bacillus.

The international Patent Application PCT/EP97/00432 proposes the recombinant production of S-layer proteins and modified S-layer proteins in the cytoplasm of Gram-negative host cells.

It has now been found, surprisingly, not only that the recombinant production of S-layer proteins is possible in the cytoplasm of Gram-negative prokaryotic host cells, but also that recombinant expression comprising integration in the outer or the cytoplasmic membrane, secretion into the periplasm or/and secretion into the extracellular space can be carried out. It has additionally been found that recombinant expression of S-layer proteins also takes place in the eukaryotic host cells.

A first aspect of the present invention is thus a process for producing S-layer proteins, which comprises (a) preparing a Gram-negative prokaryotic host cell which is transformed with a nucleic acid which codes for an S-layer protein and is operatively linked to a signal sequence which codes for a peptide which brings about integration of the S-layer protein in the outer membrane of the host cell, integration of the S-layer protein in the cytoplasmic membrane of the host cell, secretion of the S-layer protein into the periplasmic space of the host cell or/and secretion into the medium surrounding the host cell, (b) cultivating the host cell under conditions leading to expression of the nucleic acid and to production of the polypeptide encoded thereby, and (c) where appropriate isolating the resulting polypeptide from the outer membrane of the host cell, from the cytoplasmic membrane of the host cell from the periplasmic space of the host cell or/and from the medium surrounding the host cell.

A second aspect of the present invention is a process for producing S-layer proteins, which comprises (a) preparing a eukaryotic host cell which is transformed with a nucleic acid which codes for an S-layer protein and is preferably operatively linked to a signal sequence which brings about integration of the S-layer protein in the cytoplasmic membrane of the host cell, integration of the S-layer protein into an organelle of the host cell or/and secretion into the medium surrounding the host cell, (b) cultivating the host cell under conditions leading to expression of the nucleic acid and to production of the polypeptide encoded thereby, and (c) where appropriate isolating the resulting polypeptide from the cytoplasmic membrane of the host cell, from an organelle of the host cell or/and from the medium surrounding the host cell.

It has been found, surprisingly, that secretion of any heterologous S-layer proteins, including recombinant S-layer proteins, into the periplasmic space of a Gram-negative host cell or even secretion into the medium surrounding the host cell is possible. This entails the S-layer protein being formed in the periplasm of the host cell not in the form of unordered inclusion bodies but, unexpectedly, in the form of ordered monomolecular layers. In addition, anchoring of heterologous S-layer proteins in the outer or the cytoplasmic membrane of Gram-negative host cells is possible.

S-layer proteins can also be expressed in functional form in eukaryotic cells such as, for example, mammalian cells or yeast. Glycosylation takes place in the case of recombinant S-layer proteins having a eukaryotic fusion portion. In addition, glcosylation may take place in the S-layer protein portion itself.

The process according to the invention makes it possible preferably to express S-layer genes derived from B.stearothermophilus PV72, in particular to express the S-layer genes sbsA and sbsB. In addition, however, it is also possible to express S-layer genes from other organisms (cf., for example, Peyret et al., (1993) supra) by the process according to the invention.

The nucleotide sequence of the gene coding for the mature SbsA protein is indicated in SEQ ID NO. 1 from position 91–3684. The relevant amino acid sequence is depicted in SEQ ID NO. 2. The nucleotide sequence for the gene coding for the mature SbsB protein is indicated in SEQ ID NO. 5 from position 94-2763. The a relevant amino acid sequence is depicted in SEQ ID NO. 6.

In a first preferred embodiment (sbsA), the nucleic acid coding for an S-layer protein is selected from
(i) a nucleic acid which comprises the nucleotide sequence shown in SEQ ID NO. 1 from position 91 to 3684,
(ii) a nucleic acid which comprises a nucleotide sequence corresponding to the nucleic acid from (i) within the scope of the degeneracy of the genetic code, and
(iii) a nucleic acid which comprises a nucleotide sequence hybridizing with the nucleic acids from (i) or/and (ii) under stringent conditions.

In a second preferred embodiment (sbsB), the nucleic acid coding for an S-layer protein is selected from
(i) a nucleic acid which comprises the nucleotide sequence shown in SEQ ID NO. 5 from position 94 to 2763,
(ii) a nucleic acid which comprises a nucleotide sequence corresponding to the nucleic acid from (i) within the scope of the degeneracy of the genetic code, and
(iii) a nucleic acid which comprises a nucleotide sequence hybridizing with the nucleic acids from (i) or/and (ii) under stringent conditions.

The term "stringent hybridization" means for the purpose of the present invention that hybridization still occurs even after washing at 55° C., preferably 60° C., in an aqueous low-salt buffer (for example 0.2×SSC) (see also Sambrook et al. (1989), Molecular Cloning. A Laboratory Manual.

Gram-negative prokaryotic host cells are used in the first aspect of the invention. In this case, surprisingly, an S-layer protein assembled in an ordered structure is obtained in the periplasm. The host cells preferably used are enterobacteria, in particular E.coli. Examples of suitable E.coli strains are DH5α (sup E44, Δ lac U169, hsdR17, recA1, endA1, gyr A96, thi-1, rel A1; Hanahan, J. Mol. Biol. 166 (1983), 557–580) and HB 2151 (K12, ara. Δ (lac-pro), thi/F', pro A+B+, laclqZΔM15; Pharmacia Biotech).

Eukaryotic host cells are used in the second aspect of the invention. Yeast cells, mammalian cells such as, for example, CHO cells or human cells, insect cells or plant cells are preferably used.

The process according to the invention can also be employed for obtaining recombinant S-layer proteins. This is done by using a nucleic acid coding for the S-layer protein and comprising one or more insertions which code for peptide or polypeptide sequences. These insertions may, on the one hand, code only for peptides with a few amino acids, for example 1–25 amino acids. On the other hand, the insertions may also code for larger polypeptides of, for example, up to 1000 amino acids and preferably up to 500 amino acids, without the S-layer protein losing the ability to form a correctly folded structure. Besides the insertions, the recombinant S-layer protein may also comprise amino acid substitutions, in particular substitutions of single amino acids in the region of the insertion site, and, where appropriate, deletions of single amino acids or short amino acid sections of up to 30 amino acids.

Preferred insertion sites for peptide- or polypeptide-encoding sequences in the sbsA gene are regions between positions 200–3600 of the nucleotide sequence shown in SEQ ID NO. 1. Particularly preferred insertion sites are the NruI cleavage site at position 585, the PvuII cleavage site at position 881, the SnaB I cleavage site at position 920, the PvuII cleavage site at position 2507 and the PvuII cleavage site at position 2652 (PCT/EP 97/00 432). Further preferred insertion sites are positions 562, 1087, 1813, 1947, 2295, 2652, 3046, 3484 and 3594. The positions stated in each case relate to the first nucleotide of the insertion.

Preferred insertion sites into the sbsB gene are regions between positions 200–2600 of the nucleotide sequence shown in SEQ ID NO. 5. Particularly preferred insertion sites are positions 410 (codon 136), 484 (codon 161/162) and 1583 (codon 528/529) (PCT/EP 97/00432). Further preferred insertion sites are positions 598, 1012, 1435, 1808 and 2301, the position indicated in each case relating to the first nucleotide of the insertion.

The peptide- or polypeptide-encoding insertions are preferably selected from nucleotide sequences which code for cysteine residues, regions with several charged amino acids, for example Arg, Lys, Asp or Glu, or Tyr residues, DNA-binding epitopes, antigenic, allergenic or immunogenic epitopes, metal-binding epitopes, streptavidin, enzymes, cytokines or antibody-binding proteins.

A particularly preferred example of an insertion into the nucleic acid coding for the S-layer protein is a nucleotide sequence coding for streptavidin. It is possible in this way to obtain universal carrier molecules which are suitable for coupling biotinylated reagents to the integrated streptavidin of the recombinant S-layer protein and for detection in immunological or hybridization test methods.

Another preferred example of insertions comprises antigenic, allergenic or immunogenic epitopes, for example epitopes from pathogenic microorganisms such as, for example, bacteria, fungi, parasites etc. and viruses, or epitopes from plants or epitopes against endogenous substances, for example cytokines, and against toxins, in particular endotoxins. Particularly preferred examples of immunogenic epitopes are epitopes from viruses, for example from herpesviruses such as, for example herpesvirus 1, for example glycoprotein Δ, herpesvirus 6 or pseudorabiesvirus (Lomniczi et al., J. Virol. 49 (1984), 970–979), in particular epitopes from the gB, gC or/and gD genes, epitopes from foot and mouth disease virus (FMDV), in particular epitopes from the gene sections which code for VP1, VP2 or/and VP3, epitopes from flaviviruses or epitopes from filoviruses such as, for example, Ebola, Marburg or Lassa virus. The immunogenic epitopes can be selected so that they promote the generation of an antibody-mediated immune response or/and promote the generation of a cellular immune response, for example by stimulating T cells. Examples of suitable allergenic epitopes are birch pollen allergens, for example Bet v I (Ebner et al., J. Immunol. 150 (1993) 1047–1054). Also particularly preferred are antigenic epitopes able to bind and filter out, from serum or other body fluids, endogenous or exogenous substances such as, for example, cytokines or toxins. Epitopes of this type may comprise constituents of cytokine receptors or toxin receptors or of antibodies against cytokines or toxins.

Modified S-layer proteins comprising immunogenic or/and antigenic epitopes with glycosylation sites are preferably produced in eukaryotic host cells in which glycosylation is possible. It is also possible in this case for the natural S-layer sequences to be glycosylated. Examples of potential N-glycosylation sites in the S-layer gene sbsA are amino acid positions 26, 285, 343, 387, 388, 418, 421, 483, 653, 675, 902, 924, 1048, 1058, 1118, 1154 and 1161. A potential N-glycosylation may take place in the sbsB gene at positions 155, 184, 213, 302, 303, 400, 463, 606, 755 and 915. Further possible modifications of the sbsA gene comprise amidation, phosphorylation by casein kinase II, N-myristoylation and phosphorylation by protein kinase C. Further possible modifications of the sbsB gene comprise phosphorylation by cAMP- and cGMP-dependent protein kinase, phosphorylation by casein kinase II, N-myristoylation, phosphorylation by protein kinase C and attachment to a fibronectin receptor (via sequence RGD).

On the other hand, the insertions may also code for enymzes. Preferred examples are enzymes for synthe-sizing polyhydroxybutyric acid, for example PHB synthase. Incorporation of PHB synthase into the S-layer may produce, on addition of the substrate hydroxybutyric acid under suitable conditions, a molecular spinneret. Another preferred example of an enzyme is bacterial luciferase. In this case, a molecular laser can be obtained on addition of the enzyme substrate, an aldehyde, and $FMNH_2$ (reduced flavin mononucleotide), and in the presence of $O_2$.

There is likewise preference for insertions which code for cytokines such as, for example, interleukins, interferons or tumor necrosis factors. These molecules can be used, for example, in combination with immunogenic epitopes for producing vaccines.

Finally, there is also preference for insertions which code for antibody-binding proteins such as, for example, protein A or protein G or for DNA- or/and metal-binding epitopes such as, for example, leucine zippers, zinc fingers etc.

Thus, the present invention provides for the first time a Gram-negative prokaryotic cell which comprises immobilized recombinant polypeptides in native form, for example active enzymes, in the outer membrane, in the cytoplasmic membrane, preferably on the inside thereof or/and in the periplasm. It is possible in this way for 50,000–200,000,for example about 100,000, recombinant molecules to be immobilized per $mm^2$ of recombinant S-layer. Up to 3000 $m^2$ of S-layer can be obtained per kg of recombinant E.coli cells.

The present invention further provides for the first time a eukaryotic cell which comprises immobilized recombinant S-layer polypeptides in the cytoplasmic membrane, preferably on the inside thereof or/and in cell organelles such as, for example, the Golgi apparatus, lysosomes, mitochondria, chloroplasts, vacuoles or endoplasmic reticulum.

Preference is further given, in particular for secretion into the periplasm, to recombinant S-layer proteins into which cysteine residues have been incorporated. It is possible, by a selection of the insertion positions, to achieve covalent crosslinking of the S-layers in the periplasm or/and on insertion at positions unsuitable for crosslinking it is possible to provide docking sites for polypeptides, for example for enzymes, which can be covalently linked via a free SH group to the S-layer. Suitable and particularly preferred for this purpose are recombinant polypeptides into which an additional cysteine residue has been introduced by genetic manipulation methods, preferably at the N or C terminus or at a domain localized on the surface and which, through selection of a suitable expression system, are likewise secreted into the periplasm of the recombinant host cell.

In the process according to the invention, the nucleic acid coding for the S-layer protein is used operatively linked to a nucleic acid coding for a signal peptide of Gram-negative bacteria or of eukaryotic cells, i.e. the signal peptide-encoding nucleic acid is located on the 5' side of the S-layer protein-encoding nucleic acid.

On integration into the outer membrane of prokaryotic Gram-negative host cells, the C-terminal domain of the IgA protease from neisseria or haemophilus (Klauser et al., J. Mor Bio. 234 (1993), 579–593) can be used as signal peptide-encoding sequence.

On integration into the cytoplasmic membrane of Gram-negative prokaryotic host cells it is preferable to use a hydrophobic membrane-integrating protein domain which has no lytic activity and has an α-helical structure. Examples of DNA sequences which code for such a membrane-integrating protein domain are described in European patent 0 516 655.

On secretion into the periplasm of Gram-negative prokaryotic cells it is possible for the nucleic acid coding for the signal peptide to comprise (a) the signal peptide-encoding section of the nucleotide sequence depicted in SEQ ID NO. 7 and FIG. 4, (b) a nucleotide sequence corresponding to the sequence from (a) within the scope of the degeneracy of the genetic code or/and (c) a nucleotide sequence which is at least 80% and, in particular, at least 90% homologous with the sequences from (a) or/and (b). Other sequences which bring about secretion into the periplasm are described, for example, by Blondel and Bedouelle (Eur. J. Biochem 193 (1990), 325–330; Adip-Conquy et al. (Protein Eng. 8 (1995), 859–863); Weller et al (Eur. J. Biochem. 236 (1996), 34–39) and Dubreuil et al. (FEMA Immunol. Med. Microbiol. 13 (1996), 317–323).

On secretion into the extracellular medium of Gram-negative prokaryotic cells it is possible for the nucleic acid coding for the signal peptide to comprise (a) the signal peptide-encoding section of the nucleotide sequence depicted in SEQ ID NO. 8 and FIG. 5, (b) a nucleotide sequence corresponding to the sequence from (a) within the scope of the degeneracy of the genetic code or/and (c) a nucleotide sequence which is at least 80% and, in particular, at least 90% homologous with the sequences from (a) or/and (b). However, other signal peptide-encoding sequences are also suitable in addition, as described, for example, by Yuan et al. (Appl. Environ. Microbiol. 63 (1997), 263–269) and Hoogenboom et al. (Nucleic Acids Res. 19 (1991), 4133–4137).

Signal peptide-encoding nucleic acids known for expression in the cytoplasmic membrane or in organelles of eukaryotic cells are the N-terminal transit peptide of plastocyanin for transport in chloroplasts (Weisbeek et al., J. Cell. Sci. Suppl. 11 (1989), 199–223), mitochondrial signal peptides for transport in mitochondria (Skerjanc, Biochem. Cell. Biol. 68 (1990), 9–16), targeting sequences for transport in vacuoles (Vitale and Chrispeels, Bioessays 14 (1992), 151–160), targeting sequences for the cell membrane, the cytoplasm and the Golgi apparatus (Stanley, Mol. Membr. Biol. 13 (1996), 19–27), retention signals for the endoplasmic reticulum (Lencer et al., J. Cell. Biol. 131 (1995), 951–962) and transfer sequences for the Golgi apparatus or the plasma membrane (Rambourg et al., Anat. Rec. 245 (1996), 447–458).

Signal peptide-encoding nucleic acids known for secretion into the extracellular medium of eukaryotic cells are the hsp 150 delta carrier (Jamsa et al., Yeast 11 (1995), 1381–1391), the signal peptide of melittin from the honeybee (Sisk et al., J. Virol 68 (1994), 766–775), signal peptides from baculovirus (Murphy et al., Protein Expr. Purif. 4 (1993), 349–357), fragments of the K1 killer preprotoxin (Cartwright et al., Yeast 8 (1992), 261–272), the signal peptide and the N-terminal proregion of peptidylglycine α-hydroxylating monooxygenase (Mains et al., Mol. Endocrinol. 9 (1995), 3–13), the maltose-binding protein MalE with its signal sequence (Staropoli et al., J. Virol. Methods 56 (1996), 179–189;Clement and Jehanna, J. Biotechnol. 43 (1995), 169–181), the prepro-α-factor leader region of the yeast MF α1 gene (Elliot et al., Gene 79 (1989), 167–180), the signal sequence of the IL-1 receptor antagonist (Wingren et al., Cell Immunol. 169 (1996), 226–237), the signal peptide of the wheat α-amylase gene (Ribbe and Nagarajan, Mol. Gen. Genet. 235 (1992), 333–339), secretion polypeptides from fungi (Punt et al., Antonio Van Leeuwenhoek 65 (1994), 211–216), the leader peptide of the killer toxin from Kluyveromyces lactis (Baldari et al., EMBO J. 6 (1987), 229–234) and the inulinase signal sequence (Kang et al., J. Biotechnol. 48 (1996), 15–24). Fusion constructs from MalE and SbsA and from MalE and SbsB are described in the present application.

Besides the section coding for the signal peptide, the DNA sequence coding for the S-layer protein may comprise one or more sections which code for other protein domains. Such a section may preferably be located between the section coding for the signal peptide and the section coding for the S-layer protein. This section preferably codes for a secretory polypeptide from Gram-negative bacteria or eukaryotic organisms or a part thereof. A preferred example of such a nucleic acid section is the malE gene which encodes the maltose-binding protein.

In a preferred embodiment of the process according to the invention, it is also possible to express several S-layer genes in a single host cell. For this purpose there is preferably expression of at least two S-layer genes, in which case one bf them codes for a modified S-layer protein and another codes for an unmodified S-layer protein. The unmodified S-layer protein is preferably able to form an S-layer structure which is compatible with the modified S-layer protein. One example of this embodiment of the process according to the invention is an E.coli cell which is transformed with two S-layer genes, one of which is a natural sbsA or sbsB gene and the other is a recombinant sbsA or sbsB gene.

The present invention further relates to a nucleic acid which codes for an S-layer protein optionally comprising heterologous peptide or polypeptide insertions and is operatively linked to a signal sequence which codes for a peptide which brings about
  (a) integration into the outer or cytoplasmic membrane of a Gram-negative prokaryotic host cell, secretion into the periplasmic space of a Gram-negative prokaryotic host cell or/and secretion into the extra-cellular medium of a Gram-negative prokaryotic host cell, or
  (b) integration into the cytoplasmic membrane of a eukaryotic host cell, integration into an organelle of a eukaryotic host cell or/and secretion into the extracellular medium of a eukaryotic host cell.

The nucleic acid preferably codes for a recombinant S-layer protein as indicated above.

The present invention further relates to a recombinant vector which comprises at least one copy of a nucleic acid according to the invention. The vector is preferably replicable in prokaryotes or/and in eukaryotes. The vector is particularly preferably a prokaryotic or eukaryotic plasmid. It is further preferred for the vector to be the nucleic acid according to the invention operatively linked to an expression control sequence which is active in Gram-negative or eukaryotic cells. The expression control sequence particularly preferably comprises a regulable promoter. Examples of suitable prokaryotic promoters are the tac, lac, trp or λ promoter. Examples of suitable eukaryotic promoters are the SV40, CMV or metallothionein promoter.

The present invention further relates also to a host cell which is transformed with a nucleic acid or a recombinant vector according to the present invention. The cell is preferably a Gram-negative prokaryotic cell, for example an E.coli cell, or a eukaryotic cell, for example a yeast cell or a CHO cell. The cell according to the invention may comprise a recombinant S-layer structure in the cytoplasmic membrane, the periplasm or a cell organelle. Processes for the transformation of cells with nucleic acids are general prior art (see Sambrook et al., supra) and therefore need not be explained.

A recombinant S-layer structure comprising as subunit at least one recombinant S-layer protein according to the invention can be assembled from recombinant S-layer protein molecules. It is further preferred for the S-layer structure according to the invention also to comprise unmodified S-layer proteins as "diluting molecules". The unmodified S-layer proteins are preferably present in a molar proportion of 10–99% based on the total S-layer proteins.

The S-layer structure according to the invention may comprise several layers which are linked together covalently or by affinity binding. Covalent linkages can be introduced, for example, by insertions of cysteine residues and a subsequent formation of cystine bridges. Linkages by affinity binding comprise, for example, antibody-antigen, antibody-protein A or antibody-protein G or streptavidin-biotin interactions.

S-layer structures comprising recombinant S-layer proteins may also be produced where appropriate in carrier-bound form. This can be done by reassembling the S-layer structure from individual units in the presence of a peptidoglycan carrier, producing, for example, peptidoglycan layers which are covered on one or both sides with an S-layer structure. Another possibility for producing carrier-bound S-layer structures is to produce a layer of S-layers at an interface between two media, for example water/air, and to immobilize this layer on a solid phase, for example a filter membrane (cf., for example, Pum and Sleytr (1994), Thin Solid Films 244, 882–886; Küpcü et al. (1995), Biochim. Biophys. Acta 1235, 263–269).

The recombinant S-layer proteins and S-layer structures are suitable for a large number of applications. A particularly preferred use is as vaccine or adjuvant, in which case the recombinant S-layer proteins used comprise immunogenic epitopes of pathogens and/or endogenous immunostimulant polypeptides such as, for example, cytokines. Purification of the recombinant S-layer proteins is not absolutely necessary for this application. It is possible instead to use, for example, a combination with a bacterial ghost which comprises additional immunogenic epitopes where appropriate in its periplasmic space, its outer membrane or its cytoplasmic membrane.

The production of suitable "bacterial ghosts" is described, for example, in the International Patent Application PCT/EP91/00967, to which reference is made herewith. This discloses modified bacteria obtainable by transformation of a Gram-negative bacterium with the gene of a membrane protein having lytic activity from bacteriophages, with the gene of a toxin-release protein having lytic activity or with genes which comprise part-sequences thereof which code for lytic proteins, cultivation of the bacterium, expression of this lysis gene and isolation of the resulting bacterial ghost from the culture medium.

A recombinant protein which is obtainable by expression of a recombinant DNA in these Gram-negative bacteria can be bound to the membrane of these bacteria as described in European Patent 0 516 655. This recombinant DNA comprises a first DNA sequence which codes for a hydrophobic membrane-integrating protein domain which has no lytic activity, has an α-helical structure and consists of 14–20 amino acids which may be flanked N- and C-terminally by, in each case, 2–30 suitable amino acids. A second DNA sequence which codes for a required recombinant protein is operatively linked to this first DNA sequence. The Gram-negative bacterium additionally comprises a third DNA sequence which is subject to a control separate from the first and second DNA sequences and codes for a membrane protein having lytic activity from bacteriophages or a toxin-release protein having lytic activity or for the parts thereof having lytic activity. So-called "bacterial ghosts" are obtained by expression and lysis of such recombinant Gram-negative bacteria and comprise an intact surface structure with immunogenic epitopes bound to the surface.

On combination of these bacterial ghosts with recombinant S-layers according to the invention it is possible to produce vaccines and adjuvants which have particularly advantageous properties.

Another particularly preferred use of recombinant S-layer proteins and S-layer structures is the use as enzyme reactor. Such an enzyme reactor can be formed, for example, by a cell which comprises in its interior a recombinant S-layer structure according to the invention. On the other hand, the enzyme reactor may also be formed from isolated S-layer structures which have been reassembled in vitro, or combinations of various S-layer structures.

The present invention is further illustrated by the following examples and figures. These show:

SEQ ID NO. 1 the complete nucleotide sequence of the coding section of the S-layer gene sbsA of B.stearothermophilus;

SEQ ID NO. 2 the amino acid sequence derived therefrom;

SEQ ID NO. 3 the nucleotide sequence of the primer T5-X;

SEQ ID NO. 4 the nucleotide sequence of the primer E;

SEQ ID NO. 5 the complete nucleotide sequence of the coding section of the S-layer gene sbsB of B.stearothermophilus;

SEQ ID NO. 6 the amino acid sequence derived therefrom;

SEQ ID NO. 7 the signal sequence of the malE gene;

SEQ ID NO. 8 the signal sequence of gene 3 of bacteriophage fd;

FIG. 1 a diagrammatic representation of the sbsA PCR fragment used to produce the recombinant vector pBK4;

FIG. 2 a diagrammatic representation of the production of the vector pMAL-A comprising the malE-sbsA fusion gene (Example 7), FIG. 3 a diagrammatic representation of the vector pCant-A (Example 8), FIG. 4 the nucleotide sequence of an sbsA gene fused to the malE gene including its signal sequence, FIG. 5 the nucleotide sequence of an sbsA gene fused to the signal sequence of gene 3 of bacteriophage fd and FIG. 6 the nucleotide sequence of an sbsB gene fused to the malE gene including its signal sequence.

EXAMPLES

1. Bacterial Strains, Media and Plasmids

Gram-positive bacteria of the strain Bacillus stearothermophilus PV72 were cultivated in SVIII medium (Bartelmus and Perschak. Z. Zuckerind., 78 (1957), 276–281) at 58° C. E.coli bacteria were cultivated in LB medium (Sambrook et al., (1989), supra). To select transformants, ampicillin was added to the medium in a final concentration of 100 µg/ml. The plasmid pPLcAT10 (λpl, bla, colE1) (Stanssens et al., Gene 36 (1985), 211–223) was used as cloning vector.

2. Manipulation of DNA Fragments

Restriction analysis of DNA, agarose gel electrophoresis and cloning of DNA fragments were carried out by the standard methods described by Sambrook et al. (1989), supra.

The transformation of competent cells took place by electroporation using a Bio-Rad gene pulser (Bio-Rad Laboratories, Richmond, Calif., USA) in accordance with the manufacturer's protocols.

Plasmid DNA was isolated by the method of Birnboim and Doly (Nucleic Acids Res. 7 (1979), 1513–1523). Chromosomal DNA was isolated by the methods described by Ausubel et al. (Current Protocols in Molecular Biology (1987), New York, John Wiley).

Restriction endonucleases and other enzymes were purchased from Boehringer Mannheim, New England Biolabs or Strategene and were employed in accordance with the manufacturer's instructions.

3. DNA Sequencing

Sequence analysis of DNA molecules took place by the dideoxy chain-termination method of Sanger et al. The primers used for sequencing the sbsA gene were constructed on the basis of the sbsA sequence which had already been published (Kuen et al., Gene 145 (1994), 115–120).

4. PCR Amplification of sbsA

PCR amplification of the sbsA gene took place in a reaction volume of 100 µl which contained 200 µM deoxynucleotides, 1 U of Pfu polymerase (Strategene), 1×Pfu reaction buffer, 0.5 µM respective oligonucleotide primers and 100 ng of genomic DNA from B.stearothermophilus as template. The amplification was carried out over 30 cycles in a thermocycler (Biomed Thermocycler 60). Each cycle consisted of a denaturation step at 95° C. for 1.5 min, an annealing step at 56° C. for 1 min and at 50° C. for 1 min and an extension step at 72° C. for 2 min.

The primers used were the primer T5-X which is indicated in the sequence listing as SEQ ID NO. 3 and which flanks the 5' region of sbsA and comprises an XbaI site, and the primer E which is shown in the sequence listing in SEQ ID NO. 4 and which flanks the region, located 20 nucleotides downstream, of the transcription terminator of the sbsA sequence and comprises a BamHI site.

The PCR-amplified products were fractionated by electrophoresis on a 0.8% agarose gel and purified for the cloning by using the Gene Clean system (BIO101 La Jolla, Calif., USA).

5. Cloning of the sbsA Gene into the Vector pPLcAT10

The sbsA gene with a length of 3.79 kb obtained by PCR was purified and cleaved with the restriction endonucleases XbaI and BamHI. The resulting XBaI-BamHI fragment was cloned into the corresponding restriction sites of the vector pPLcAT10 so that the sbsA gene was under the transcriptional control of the pL promoter located upstream. The ATG start codon of the sbsA sequence was reconstructed by the cloning procedure. The cloned sbsA sequence comprised the N-terminal signal sequence of sbsA and terminated 20 nt after the transcription terminator. After ligation of the vector DNA with the sbsA fragment, the E.coli strain pop2135 (DSM 10509) was transformed by electrotransformation. The resulting clones were subjected to a DNA restriction analysis. One positive clone was sequenced in order to verify the correct sequence junctions at the 5' and 3' ends. This clone was called pBK4.

A diagrammatic representation of the 3.79 kb XbaI sbsA fragment and its location in the multiple cloning site of the plasmid pBK4 is depicted in FIG. 1 (abbreviations: tT:

transcription terminator; ori: origin of DNA replication; amp: ampicillin-resistance gene).

6. Recombinant Expression of the sbsA Gene in the Cytoplasm of E.coli (Comparative Example)

E.coli pop2135/pBK4 cells were cultivated at 28° C. until the optical density $OD_{600}$ reached 0.3. The expression of sbsA was then induced by increasing the cultivation temperature from 28° C. to 42°C. 1.5 ml aliquots were taken before and 1, 2, 3 and 5 hours after induction of sbsA expression. The controls used were E.coli pop2135/pPLcAT10 (cultivated under the same conditions) and B.stearothermophilus PV72.

Culture supernatants and cell extracts from all the samples were investigated for expression of the S-layer protein by SDS-PAGE and Western immunoblotting.

For the Western blot, the proteins were transferred to a nitrocellulose membrane and incubated with a rabbit polyclonal antiserum against SbsA. The production of this antiserum is described by Egelseer et al. (J. Bacteriol. 177 (1995), 1444–1451). A conjugate of goat anti-rabbit IgG and alkaline phosphatase was used to detect bound SbsA-specific antibodies.

An additional strong protein band with approximately the same molecular weight as the wild-type SbsA protein was found in cytoplasmic extracts from E.coli cells transformed with pBK4.

No SbsA protein was detectable in supernatants of E.coli cells transformed with pBK4, even after induction of sbsA gene expression. It is evident from this that SbsA is not exported into the surrounding medium.

7. Secretion of the SbsA Protein into the Periplasm

The sbsA gene was cloned without signal sequence and with stop codon at the 3' end into the polylinker of the commercially available plasmid pMAL-P2 (New England Biolabs) (FIG. 2). The resulting plasmid pMAL-A comprises, under the control of the taq promoter, a fusion gene comprising the malE gene including its signal sequence, and the sbsA gene without its signal sequence. A factor Xa cleavage site is located between the two domains.

Analysis of the crude extract of E.coli DH5α cells (Hanahan (1983) supra) transformed with pMAL-A showed expression of a MalE-SbsA fusion polypeptide with a molecular weight of about 170 kDa in the periplasmic fraction, which was produced by a cold osmotic shock procedure (Neu and Heppel, J. Biol. Chem. 240 (1965); 3685–2692), of the cell extract. The nucleotide sequence of the malE-sbsA fusion gene is depicted in FIG. 4. The malE signal sequence is shown in SEQ ID NO. 7.

8. Secretion of the SbsA Protein into the Extracellular Space

The plasmid pCant-A was produced by cloning the sbsA gene without its own signal sequence and with stop codon at the 3' end into the commercially available plasmid pCANTAB5E (Pharmacia Biotech) which had been cut with SfiI and NotI. It comprises, under the control of the lac promoter (Plac), the signal sequence of gene 3 of bacteriophage fd (45 nt) fused to the sbsA gene without its own signal sequence (FIG. 3). The nucleotide sequence of the fusion gene is depicted in FIG. 5. The fd gene 3 signal sequence is shown in SEQ ID NO. 8.

The SbsA protein was detectable in the culture supernatant from E.coli HB2151 cells (Pharmacia Biotech) transformed with pCant-A.

9. Secretion of the SbsB Protein into the Periplasm and into the Extracellular Space The sbsB gene was cloned, as described in Examples 7 and 8, without its own signal sequence, into the plasmids pMAL-P2 and pCANTAB5E, resulting in the plasmids pMAL-8 and pCant-B.

Secretion of the sbsB protein into the periplasm and into the extracellular space was demonstrable in E.coli cells transformed with the plasmids pMAL-B and pCant-B.

---

What is claimed is:

1. A process for producing S-layer proteins, which comprises
   (a) preparing a Gram-negative prokaryotic host cell which is transformed with a nucleic acid which codes for an S-layer protein from a non-Gram negative bacteria and is operatively linked to a signal sequence which codes for a peptide which brings about integration of the S-layer protein in the outer membrane of the host cell, integration of the S-layer protein in the cytoplasmic membrane of the host cell, secretion of the S-layer protein into the periplasmic space of the host cell or/and secretion into the medium surrounding the host cell,
   (b) cultivating the host cell under conditions leading to expression of the nucleic acid and to production of the polypeptide encoded thereby, and
   (c) where appropriate isolating the resulting polypeptide from the outer membrane of the host cell, from the cytoplasmic membrane of the host cell from the periplasmic space of the host cell or/and from the medium surrounding the host cell.

2. A process as claimed in claim 1, wherein an *Esherichia coli* host cell is used.

3. A process as claimed in claim 1, wherein the nucleic acid which codes for an S-layer protein, codes for a self assembling S-layer protein and is selected from
   (i) a nucleic acid encoding a SbsA protein wherein said nucleic acid comprises the nucleotide sequence shown in SEQ ID NO: 1 from position 91 to 3684,
   (ii) a nucleic acid which comprises a nucleotide sequence corresponding to the nucleic acid from (i) within the scope of the degeneracy of the genetic code, and
   (iii) a nucleic acid comprising a nucleotide sequence which hybridizes with a nucleic acid sequence which is complementary to the nucleic acids from (i) and/or (ii) after washing at 55° C. in 0.2×SSC buffer.

4. A process as claimed in claim 1, wherein the nucleic acid coding for the S-layer protein comprises one or more insertions which code for heterologous peptide or polypeptide sequences.

5. A process as claimed in claim 4, wherein the insertion site is located at one or more positions selected from the group consisting of position 562, 585, 881, 920, 1087, 1813, 1947, 2295, 2652, 3046, 3484, and 3594 of the nucleotide sequence shown in SEQ ID NO:1.

6. A process as claimed in claim 4, wherein the insertions are selected from nucleotide sequences which code for cysteine residues, regions with several charged amino acids or Tyr residues, DNA-binding epitopes, metal-binding epitopes, immunogenic epitopes, allergenic epitopes, antigenic epitopes, streptavidin, enzymes, cytokines or antibody-binding proteins.

7. A process as claimed in claim 6, wherein the insertions code for immunogenic epitopes from herpes viruses, FMDV, flaviviruses or filoviruses.

8. A process as claimed in claim 1, wherein an operatively linked nucleic acid which codes for a signal peptide from Gram-negative prokaryotic cells is located on the 5' side of the nucleic acid coding for the S-layer protein.

9. A process as claimed in claim 8, wherein the nucleic acid coding for the signal peptide comprises
   (a) the signal peptide encoding section of the nucleotide sequence depicted in SEQ ID NO: 7 or 8,
   (b) a nucleotide sequence corresponding to the sequence from (a) within the scope of degeneracy of the genetic code or/and
   (c) a nucleotide sequence which is at least 80% homologous with the sequence from (a) or (b).

10. A process as claimed in claim 1, wherein at least two S-layer genes are expressed in the host cell, one of which codes for a modified S-layer protein and another codes for an unmodified S-layer protein.

11. A process as claimed in claim 10, wherein the modified S-layer protein is able to form an S-layer structure which is compatible with the unmodified S-layer protein.

12. The process according to claim 6, wherein said herpes viruses is selected from the group consisting of herpes viruses 1 and 6.

\* \* \* \* \*

SEQUENCE LISTING

```
<160> NUMBER OF SEQ ID NOS:  13

<210> SEQ ID NO 1
<211> LENGTH: 3687
<212> TYPE: DNA
<213> ORGANISM: Bacillus stearothermophilus
<220> FEATURE:
<221> NAME/KEY: CDS
<222> LOCATION: (1)..(3684)
<221> NAME/KEY: sig_peptide
<222> LOCATION: (1)..(90)
<221> NAME/KEY: mat_peptide
<222> LOCATION: (91)..(3684)

<400> SEQUENCE: 1 atg gat agg aaa aaa gct gtg aaa cta gca aca gca agt gct att gca      48
Met Asp Arg Lys Lys Ala Val Lys Leu Ala Thr Ala Ser Ala Ile Ala
-30                 -25                 -20                 -15 gca agt gca ttt gtc gct gca aat cca aac gct tct gaa gcg gct aca      96
Ala Ser Ala Phe Val Ala Ala Asn Pro Asn Ala Ser Glu Ala Ala Thr
                -10                 -5                  -1   1 gat gta gca aca gta gta agc caa gca aaa gca cag ttc aaa aaa gca     144
```

```
Asp Val Ala Thr Val Val Ser Gln Ala Lys Ala Gln Phe Lys Lys Ala
        5                   10                  15 tac tat act tac agc cat aca gta acg gaa act ggt gaa ttc cca aac        192
Tyr Tyr Thr Tyr Ser His Thr Val Thr Glu Thr Gly Glu Phe Pro Asn
 20                  25                  30 att aac gat gta tat gct gaa tac aac aaa gcg aaa aaa cga tac cgt        240
Ile Asn Asp Val Tyr Ala Glu Tyr Asn Lys Ala Lys Lys Arg Tyr Arg
 35                  40                  45                  50 gat gcg gta gca tta gtg aat aaa gca ggt ggc gcg aaa aaa gac gct        288
Asp Ala Val Ala Leu Val Asn Lys Ala Gly Gly Ala Lys Lys Asp Ala
                 55                  60                  65 tac tta gct gat tta caa aaa gaa tat gaa act tac gtt ttc aaa gca        336
Tyr Leu Ala Asp Leu Gln Lys Glu Tyr Glu Thr Tyr Val Phe Lys Ala
             70                  75                  80 aac cct aaa tct ggc gaa gct cgt gta gca act tac atc gat gct tac        384
Asn Pro Lys Ser Gly Glu Ala Arg Val Ala Thr Tyr Ile Asp Ala Tyr
         85                  90                  95 aac tat gca aca aaa tta gac gaa atg cgc caa gag cta gag gct gct        432
Asn Tyr Ala Thr Lys Leu Asp Glu Met Arg Gln Glu Leu Glu Ala Ala
    100                 105                 110 gtt caa gca aaa gat tta gaa aaa gca gaa caa tac tat cac aaa att        480
Val Gln Ala Lys Asp Leu Glu Lys Ala Glu Gln Tyr Tyr His Lys Ile
115                 120                 125                 130 cct tat gaa att aaa act cgc aca gtc att tta gat cgc gta tat ggt        528
Pro Tyr Glu Ile Lys Thr Arg Thr Val Ile Leu Asp Arg Val Tyr Gly
                135                 140                 145 aaa aca act cgt gat tta ctt cgc tct aca ttt aaa gca aaa gca caa        576
Lys Thr Thr Arg Asp Leu Leu Arg Ser Thr Phe Lys Ala Lys Ala Gln
            150                 155                 160 gaa ctt cgc gac agc tta att tat gat att acc gtt gca atg aaa gcg        624
Glu Leu Arg Asp Ser Leu Ile Tyr Asp Ile Thr Val Ala Met Lys Ala
        165                 170                 175 cgc gaa gta caa gac gct gtg aaa gca ggc aat tta gac aaa gct aaa        672
Arg Glu Val Gln Asp Ala Val Lys Ala Gly Asn Leu Asp Lys Ala Lys
    180                 185                 190 gct gct gtt gat caa atc aat caa tac tta cca aaa gta aca gat gct        720
Ala Ala Val Asp Gln Ile Asn Gln Tyr Leu Pro Lys Val Thr Asp Ala
195                 200                 205                 210 ttc aaa act gaa cta aca gaa gta gcg aaa aaa gca tta gat gca gat        768
Phe Lys Thr Glu Leu Thr Glu Val Ala Lys Lys Ala Leu Asp Ala Asp
                215                 220                 225 gaa gct gcg ctt act cca aaa gtt gaa agt gta agt gcg att aac act        816
Glu Ala Ala Leu Thr Pro Lys Val Glu Ser Val Ser Ala Ile Asn Thr
            230                 235                 240 caa aac aaa gct gtt gaa tta aca gca gta cca gtg aac gga aca cta        864
Gln Asn Lys Ala Val Glu Leu Thr Ala Val Pro Val Asn Gly Thr Leu
        245                 250                 255 aaa tta caa ctt tca gct gct gca aat gaa gat aca gta aac gta aat        912
Lys Leu Gln Leu Ser Ala Ala Ala Asn Glu Asp Thr Val Asn Val Asn
    260                 265                 270 act gta cgt atc tat aaa gtg gac ggt aac att cca ttt gcc ctt aat        960
Thr Val Arg Ile Tyr Lys Val Asp Gly Asn Ile Pro Phe Ala Leu Asn
275                 280                 285                 290 acg gca gat gtt tct tta tct aca gac gga aaa act atc act gtg gat       1008
Thr Ala Asp Val Ser Leu Ser Thr Asp Gly Lys Thr Ile Thr Val Asp
                295                 300                 305 gct tca act cca ttc gaa aat aat acg gag tat aaa gta gta gtt aaa       1056
Ala Ser Thr Pro Phe Glu Asn Asn Thr Glu Tyr Lys Val Val Val Lys
            310                 315                 320
```

```
ggt att aaa gac aaa aat ggc aaa gaa ttt aaa gaa gat gca ttc act      1104
Gly Ile Lys Asp Lys Asn Gly Lys Glu Phe Lys Glu Asp Ala Phe Thr
        325                 330                 335 ttc aag ctt cga aat gat gct gta gtt act caa gtg ttt gga act aat      1152
Phe Lys Leu Arg Asn Asp Ala Val Val Thr Gln Val Phe Gly Thr Asn
        340                 345                 350 gta aca aac aac act tct gta aac tta gca gca ggt act ttc gac act      1200
Val Thr Asn Asn Thr Ser Val Asn Leu Ala Ala Gly Thr Phe Asp Thr
355                 360                 365                 370 gac gat act tta aca gta gta ttt gat aag ttg tta gca cct gaa act      1248
Asp Asp Thr Leu Thr Val Val Phe Asp Lys Leu Leu Ala Pro Glu Thr
                375                 380                 385 gta aac agc tcg aac gtt act att aca gat gtt gaa act gga aaa cgc      1296
Val Asn Ser Ser Asn Val Thr Ile Thr Asp Val Glu Thr Gly Lys Arg
        390                 395                 400 att cca gta att gca tct act tct ggt tct aca att act att acg tta      1344
Ile Pro Val Ile Ala Ser Thr Ser Gly Ser Thr Ile Thr Ile Thr Leu
            405                 410                 415 aaa gaa gcg tta gta act ggt aaa caa tat aaa ctt gct atc aat aat      1392
Lys Glu Ala Leu Val Thr Gly Lys Gln Tyr Lys Leu Ala Ile Asn Asn
    420                 425                 430 gtt aaa aca tta act ggt tac aat gca gaa gct tac gag tta gtg ttc      1440
Val Lys Thr Leu Thr Gly Tyr Asn Ala Glu Ala Tyr Glu Leu Val Phe
435                 440                 445                 450 act gca aac gca tca gca cca act gtt gct acc gct cct act act tta      1488
Thr Ala Asn Ala Ser Ala Pro Thr Val Ala Thr Ala Pro Thr Thr Leu
                455                 460                 465 ggt ggt aca act tta tct act ggt tct ctt aca aca aat gtt tgg ggt      1536
Gly Gly Thr Thr Leu Ser Thr Gly Ser Leu Thr Thr Asn Val Trp Gly
        470                 475                 480 aaa ttg gct ggt ggt gtg aat gaa gct gga act tat tat cct ggt ctt      1584
Lys Leu Ala Gly Gly Val Asn Glu Ala Gly Thr Tyr Tyr Pro Gly Leu
            485                 490                 495 caa ttc aca aca acg ttt gct act aag tta gac gaa tct act tta gct      1632
Gln Phe Thr Thr Thr Phe Ala Thr Lys Leu Asp Glu Ser Thr Leu Ala
    500                 505                 510 gat aac ttt gta tta gtt gaa aaa gaa tct ggt aca gtt gtt gct tct      1680
Asp Asn Phe Val Leu Val Glu Lys Glu Ser Gly Thr Val Val Ala Ser
515                 520                 525                 530 gaa cta aaa tat aat gca gac gct aaa atg gta act tta gtg cca aaa      1728
Glu Leu Lys Tyr Asn Ala Asp Ala Lys Met Val Thr Leu Val Pro Lys
                535                 540                 545 gcg gac ctt aaa gaa aat aca atc tat caa atc aaa att aaa aaa ggc      1776
Ala Asp Leu Lys Glu Asn Thr Ile Tyr Gln Ile Lys Ile Lys Lys Gly
        550                 555                 560 ttg aag tcc gat aaa ggt att gaa tta ggc act gtt aac gag aaa aca      1824
Leu Lys Ser Asp Lys Gly Ile Glu Leu Gly Thr Val Asn Glu Lys Thr
            565                 570                 575 tat gag ttc aaa act caa gac tta act gct cct aca gtt att agc gta      1872
Tyr Glu Phe Lys Thr Gln Asp Leu Thr Ala Pro Thr Val Ile Ser Val
    580                 585                 590 acg tct aaa aat ggc gac gct gga tta aaa gta act gaa gct caa gaa      1920
Thr Ser Lys Asn Gly Asp Ala Gly Leu Lys Val Thr Glu Ala Gln Glu
595                 600                 605                 610 ttt act gtg aag ttc tca gag aat tta aat aca ttt aat gct aca acc      1968
Phe Thr Val Lys Phe Ser Glu Asn Leu Asn Thr Phe Asn Ala Thr Thr
                615                 620                 625 gtt tcg ggt agc aca atc aca tac ggt caa gtt gct gta gta aaa gcg      2016
Val Ser Gly Ser Thr Ile Thr Tyr Gly Gln Val Ala Val Val Lys Ala
        630                 635                 640
```

-continued

```
ggt gca aac tta tct gct ctt aca gca agt gac atc att cca gct agt      2064
Gly Ala Asn Leu Ser Ala Leu Thr Ala Ser Asp Ile Ile Pro Ala Ser
        645                 650                 655 gtt gaa gcg gtt act ggt caa gat gga aca tac aaa gtg aaa gtt gct      2112
Val Glu Ala Val Thr Gly Gln Asp Gly Thr Tyr Lys Val Lys Val Ala
660                 665                 670 gct aac caa tta gaa cgt aac caa ggg tac aaa tta gta gtg ttc ggt      2160
Ala Asn Gln Leu Glu Arg Asn Gln Gly Tyr Lys Leu Val Val Phe Gly
675                 680                 685                 690 aaa ggt gca aca gct cct gtt aaa gat gct gca aat gca aat act tta      2208
Lys Gly Ala Thr Ala Pro Val Lys Asp Ala Ala Asn Ala Asn Thr Leu
            695                 700                 705 gca act aac tat atc tat aca ttt aca act gaa ggt caa gac gta aca      2256
Ala Thr Asn Tyr Ile Tyr Thr Phe Thr Thr Glu Gly Gln Asp Val Thr
        710                 715                 720 gca cca acg gtt aca aaa gta ttc aaa ggt gat tct tta aaa gac gct      2304
Ala Pro Thr Val Thr Lys Val Phe Lys Gly Asp Ser Leu Lys Asp Ala
    725                 730                 735 gat gca gtt act aca ctt acg aac gtt gat gca ggt caa aaa ttc act      2352
Asp Ala Val Thr Thr Leu Thr Asn Val Asp Ala Gly Gln Lys Phe Thr
740                 745                 750 atc caa ttt agc gaa gaa tta aaa act tct agt ggt tct tta gtg ggt      2400
Ile Gln Phe Ser Glu Glu Leu Lys Thr Ser Ser Gly Ser Leu Val Gly
755                 760                 765                 770 ggc aaa gta act gtc gag aaa tta aca aac aac gga tgg gta gat gct      2448
Gly Lys Val Thr Val Glu Lys Leu Thr Asn Asn Gly Trp Val Asp Ala
            775                 780                 785 ggt act gga aca act gta tca gtt gct cct aag aca gat gca aat ggt      2496
Gly Thr Gly Thr Thr Val Ser Val Ala Pro Lys Thr Asp Ala Asn Gly
        790                 795                 800 aaa gta aca gct gct gtg gtt aca tta act ggt ctt gac aat aac gac      2544
Lys Val Thr Ala Ala Val Val Thr Leu Thr Gly Leu Asp Asn Asn Asp
    805                 810                 815 aaa gat gcg aaa ttg cgt ctg gta gta gat aag tct tct act gat gga      2592
Lys Asp Ala Lys Leu Arg Leu Val Val Asp Lys Ser Ser Thr Asp Gly
820                 825                 830 att gct gat gta gct ggt aat gta att aag gaa aaa gat att tta att      2640
Ile Ala Asp Val Ala Gly Asn Val Ile Lys Glu Lys Asp Ile Leu Ile
835                 840                 845                 850 cgt tac aac agc tgg aga cac act gta gct tct gtg aaa gct gct gct      2688
Arg Tyr Asn Ser Trp Arg His Thr Val Ala Ser Val Lys Ala Ala Ala
            855                 860                 865 gac aaa gat ggt caa aac gct tct gct gca ttc cca aca agc act gca      2736
Asp Lys Asp Gly Gln Asn Ala Ser Ala Ala Phe Pro Thr Ser Thr Ala
        870                 875                 880 att gat aca act aag agc tta tta gtt gaa ttc aat gaa act gat tta      2784
Ile Asp Thr Thr Lys Ser Leu Leu Val Glu Phe Asn Glu Thr Asp Leu
    885                 890                 895 gcg gaa gtt aaa cct gag aac atc gtt gtt aaa gat gca gca ggt aat      2832
Ala Glu Val Lys Pro Glu Asn Ile Val Val Lys Asp Ala Ala Gly Asn
900                 905                 910 gcg gta gct ggt act gta aca gca tta gac ggt tct aca aat aaa ttt      2880
Ala Val Ala Gly Thr Val Thr Ala Leu Asp Gly Ser Thr Asn Lys Phe
915                 920                 925                 930 gta ttc act cca tct caa gaa tta aaa gct ggt aca gtt tac tct gta      2928
Val Phe Thr Pro Ser Gln Glu Leu Lys Ala Gly Thr Val Tyr Ser Val
            935                 940                 945 aca att gac ggt gtg aga gat aaa gta ggt aac aca atc tct aaa tac      2976
Thr Ile Asp Gly Val Arg Asp Lys Val Gly Asn Thr Ile Ser Lys Tyr
```

-continued

```
                     950                 955                 960
att act tcg ttc aag act gta tct gcg aat cca acg tta tct tca atc         3024
Ile Thr Ser Phe Lys Thr Val Ser Ala Asn Pro Thr Leu Ser Ser Ile
            965                 970                 975 agc att gct gac ggt gca gtt aac gtt gac cgt tct aaa aca att aca         3072
Ser Ile Ala Asp Gly Ala Val Asn Val Asp Arg Ser Lys Thr Ile Thr
    980                 985                 990 att gaa ttc agc gat tca gtt cca aac cca aca atc act ctt aag aag         3120
Ile Glu Phe Ser Asp Ser Val Pro Asn Pro Thr Ile Thr Leu Lys Lys
995                 1000                1005                1010 gct gac gga act tca ttt act aat tac act tta gta aat gta aat aat         3168
Ala Asp Gly Thr Ser Phe Thr Asn Tyr Thr Leu Val Asn Val Asn Asn
                1015                1020                1025 gaa aat aaa aca tac aaa att gta ttc cac aaa ggt gta aca ctt gac         3216
Glu Asn Lys Thr Tyr Lys Ile Val Phe His Lys Gly Val Thr Leu Asp
            1030                1035                1040 gag ttt act caa tat gag tta gca gtt tca aaa gat ttt caa act ggt         3264
Glu Phe Thr Gln Tyr Glu Leu Ala Val Ser Lys Asp Phe Gln Thr Gly
        1045                1050                1055 act gat att gat agc aaa gtt aca ttc atc aca ggt tct gtt gct act         3312
Thr Asp Ile Asp Ser Lys Val Thr Phe Ile Thr Gly Ser Val Ala Thr
    1060                1065                1070 gac gaa gta aaa cct gct cta gta ggc gtt ggt tca tgg aat gga aca         3360
Asp Glu Val Lys Pro Ala Leu Val Gly Val Gly Ser Trp Asn Gly Thr
1075                1080                1085                1090 agc tat act cag gat gct gca gca aca cga ctt cgg tct gta gct gac         3408
Ser Tyr Thr Gln Asp Ala Ala Ala Thr Arg Leu Arg Ser Val Ala Asp
                1095                1100                1105 ttc gtt gcg gag cca gtt gcc ctt caa ttc tca gaa ggt atc gat tta         3456
Phe Val Ala Glu Pro Val Ala Leu Gln Phe Ser Glu Gly Ile Asp Leu
            1110                1115                1120 acg aat gca act gtg aca gta aca aat att act gat gat aaa act gtt         3504
Thr Asn Ala Thr Val Thr Val Thr Asn Ile Thr Asp Asp Lys Thr Val
        1125                1130                1135 gaa gtt att tca aaa gag agt gta gac gca gac cat gat gca ggt gct         3552
Glu Val Ile Ser Lys Glu Ser Val Asp Ala Asp His Asp Ala Gly Ala
    1140                1145                1150 act aag gag aca tta gta att aac aca gtt act cct tta gta ctt gat         3600
Thr Lys Glu Thr Leu Val Ile Asn Thr Val Thr Pro Leu Val Leu Asp
1155                1160                1165                1170 aac agc aag act tat aag att gta gta agt gga gtt aaa gat gca gca         3648
Asn Ser Lys Thr Tyr Lys Ile Val Val Ser Gly Val Lys Asp Ala Ala
                1175                1180                1185 ggt aat gtt gca gat act att aca ttc tat att aag taa                      3687
Gly Asn Val Ala Asp Thr Ile Thr Phe Tyr Ile Lys
            1190                1195

<210> SEQ ID NO 2
<211> LENGTH: 1228
<212> TYPE: PRT
<213> ORGANISM: Bacillus stearothermophilus

<400> SEQUENCE: 2

Met Asp Arg Lys Lys Ala Val Lys Leu Ala Thr Ala Ser Ala Ile Ala
-30                 -25                 -20                 -15

Ala Ser Ala Phe Val Ala Ala Asn Pro Asn Ala Ser Glu Ala Ala Thr
                -10                 -5                  -1  1

Asp Val Ala Thr Val Val Ser Gln Ala Lys Ala Gln Phe Lys Lys Ala
        5                   10                  15
```

-continued

```
Tyr Tyr Thr Tyr Ser His Thr Val Thr Glu Thr Gly Glu Phe Pro Asn
         20                  25                  30

Ile Asn Asp Val Tyr Ala Glu Tyr Asn Lys Ala Lys Lys Arg Tyr Arg
 35                  40                  45                  50

Asp Ala Val Ala Leu Val Asn Lys Ala Gly Ala Lys Lys Asp Ala
                 55                  60                  65

Tyr Leu Ala Asp Leu Gln Lys Glu Tyr Glu Thr Tyr Val Phe Lys Ala
                 70                  75                  80

Asn Pro Lys Ser Gly Glu Ala Arg Val Ala Thr Tyr Ile Asp Ala Tyr
             85                  90                  95

Asn Tyr Ala Thr Lys Leu Asp Glu Met Arg Gln Glu Leu Glu Ala Ala
            100                 105                 110

Val Gln Ala Lys Asp Leu Glu Lys Ala Glu Gln Tyr Tyr His Lys Ile
115                 120                 125                 130

Pro Tyr Glu Ile Lys Thr Arg Thr Val Ile Leu Asp Arg Val Tyr Gly
                135                 140                 145

Lys Thr Thr Arg Asp Leu Leu Arg Ser Thr Phe Lys Ala Lys Ala Gln
                150                 155                 160

Glu Leu Arg Asp Ser Leu Ile Tyr Asp Ile Thr Val Ala Met Lys Ala
            165                 170                 175

Arg Glu Val Gln Asp Ala Val Lys Ala Gly Asn Leu Asp Lys Ala Lys
180                 185                 190

Ala Ala Val Asp Gln Ile Asn Gln Tyr Leu Pro Lys Val Thr Asp Ala
195                 200                 205                 210

Phe Lys Thr Glu Leu Thr Glu Val Ala Lys Lys Ala Leu Asp Ala Asp
                215                 220                 225

Glu Ala Ala Leu Thr Pro Lys Val Glu Ser Val Ser Ala Ile Asn Thr
                230                 235                 240

Gln Asn Lys Ala Val Glu Leu Thr Ala Val Pro Val Asn Gly Thr Leu
            245                 250                 255

Lys Leu Gln Leu Ser Ala Ala Asn Glu Asp Thr Val Asn Val Asn
260                 265                 270

Thr Val Arg Ile Tyr Lys Val Asp Gly Asn Ile Pro Phe Ala Leu Asn
275                 280                 285                 290

Thr Ala Asp Val Ser Leu Ser Thr Asp Gly Lys Thr Ile Thr Val Asp
                295                 300                 305

Ala Ser Thr Pro Phe Glu Asn Asn Thr Glu Tyr Lys Val Val Lys
                310                 315                 320

Gly Ile Lys Asp Lys Asn Gly Lys Glu Phe Lys Glu Asp Ala Phe Thr
            325                 330                 335

Phe Lys Leu Arg Asn Asp Ala Val Val Thr Gln Val Phe Gly Thr Asn
340                 345                 350

Val Thr Asn Asn Thr Ser Val Asn Leu Ala Ala Gly Thr Phe Asp Thr
355                 360                 365                 370

Asp Asp Thr Leu Thr Val Val Phe Asp Lys Leu Leu Ala Pro Glu Thr
                375                 380                 385

Val Asn Ser Ser Asn Val Thr Ile Thr Asp Val Glu Thr Gly Lys Arg
            390                 395                 400

Ile Pro Val Ile Ala Ser Ser Gly Ser Thr Ile Thr Ile Thr Leu
            405                 410                 415

Lys Glu Ala Leu Val Thr Gly Lys Gln Tyr Lys Leu Ala Ile Asn Asn
420                 425                 430

Val Lys Thr Leu Thr Gly Tyr Asn Ala Glu Ala Tyr Glu Leu Val Phe
```

-continued

```
435                 440                 445                 450
Thr Ala Asn Ala Ser Ala Pro Thr Val Ala Thr Ala Pro Thr Thr Leu
                455                 460                 465
Gly Gly Thr Thr Leu Ser Thr Gly Ser Leu Thr Thr Asn Val Trp Gly
                470                 475                 480
Lys Leu Ala Gly Gly Val Asn Glu Ala Gly Thr Tyr Tyr Pro Gly Leu
                485                 490                 495
Gln Phe Thr Thr Thr Phe Ala Thr Lys Leu Asp Glu Ser Thr Leu Ala
                500                 505                 510
Asp Asn Phe Val Leu Val Glu Lys Glu Ser Gly Thr Val Val Ala Ser
515                 520                 525                 530
Glu Leu Lys Tyr Asn Ala Asp Ala Lys Met Val Thr Leu Val Pro Lys
                535                 540                 545
Ala Asp Leu Lys Glu Asn Thr Ile Tyr Gln Ile Lys Ile Lys Lys Gly
                550                 555                 560
Leu Lys Ser Asp Lys Gly Ile Glu Leu Gly Thr Val Asn Glu Lys Thr
                565                 570                 575
Tyr Glu Phe Lys Thr Gln Asp Leu Thr Ala Pro Thr Val Ile Ser Val
                580                 585                 590
Thr Ser Lys Asn Gly Asp Ala Gly Leu Lys Val Thr Glu Ala Gln Glu
595                 600                 605                 610
Phe Thr Val Lys Phe Ser Glu Asn Leu Asn Thr Phe Asn Ala Thr Thr
                615                 620                 625
Val Ser Gly Ser Thr Ile Thr Tyr Gly Gln Val Ala Val Lys Ala
                630                 635                 640
Gly Ala Asn Leu Ser Ala Leu Thr Ala Ser Asp Ile Ile Pro Ala Ser
                645                 650                 655
Val Glu Ala Val Thr Gly Gln Asp Gly Thr Tyr Lys Val Lys Val Ala
                660                 665                 670
Ala Asn Gln Leu Glu Arg Asn Gln Gly Tyr Lys Leu Val Val Phe Gly
675                 680                 685                 690
Lys Gly Ala Thr Ala Pro Val Lys Asp Ala Ala Asn Ala Asn Thr Leu
                695                 700                 705
Ala Thr Asn Tyr Ile Tyr Thr Phe Thr Thr Glu Gly Gln Asp Val Thr
                710                 715                 720
Ala Pro Thr Val Thr Lys Val Phe Lys Gly Asp Ser Leu Lys Asp Ala
                725                 730                 735
Asp Ala Val Thr Thr Leu Thr Asn Val Asp Ala Gly Gln Lys Phe Thr
740                 745                 750
Ile Gln Phe Ser Glu Glu Leu Lys Thr Ser Ser Gly Ser Leu Val Gly
755                 760                 765                 770
Gly Lys Val Thr Val Glu Lys Leu Thr Asn Asn Gly Trp Val Asp Ala
                775                 780                 785
Gly Thr Gly Thr Thr Val Ser Val Ala Pro Lys Thr Asp Ala Asn Gly
                790                 795                 800
Lys Val Thr Ala Ala Val Val Thr Leu Thr Gly Leu Asp Asn Asn Asp
                805                 810                 815
Lys Asp Ala Lys Leu Arg Leu Val Val Asp Lys Ser Ser Thr Asp Gly
                820                 825                 830
Ile Ala Asp Val Ala Gly Asn Val Ile Lys Glu Lys Asp Ile Leu Ile
835                 840                 845                 850
Arg Tyr Asn Ser Trp Arg His Thr Val Ala Ser Val Lys Ala Ala Ala
                855                 860                 865
```

Asp Lys Asp Gly Gln Asn Ala Ser Ala Ala Phe Pro Thr Ser Thr Ala
          870                 875                 880

Ile Asp Thr Thr Lys Ser Leu Leu Val Glu Phe Asn Glu Thr Asp Leu
          885                 890                 895

Ala Glu Val Lys Pro Glu Asn Ile Val Lys Asp Ala Ala Gly Asn
    900                 905                 910

Ala Val Ala Gly Thr Val Thr Ala Leu Asp Gly Ser Thr Asn Lys Phe
915                 920                 925                 930

Val Phe Thr Pro Ser Gln Glu Leu Lys Ala Gly Thr Val Tyr Ser Val
              935                 940                 945

Thr Ile Asp Gly Val Arg Asp Lys Val Gly Asn Thr Ile Ser Lys Tyr
              950                 955                 960

Ile Thr Ser Phe Lys Thr Val Ser Ala Asn Pro Thr Leu Ser Ser Ile
          965                 970                 975

Ser Ile Ala Asp Gly Ala Val Asn Val Asp Arg Ser Lys Thr Ile Thr
          980                 985                 990

Ile Glu Phe Ser Asp Ser Val Pro Asn Pro Thr Ile Thr Leu Lys Lys
995                 1000                1005                1010

Ala Asp Gly Thr Ser Phe Thr Asn Tyr Thr Leu Val Asn Val Asn Asn
              1015                1020                1025

Glu Asn Lys Thr Tyr Lys Ile Val Phe His Lys Gly Val Thr Leu Asp
              1030                1035                1040

Glu Phe Thr Gln Tyr Glu Leu Ala Val Ser Lys Asp Phe Gln Thr Gly
        1045                1050                1055

Thr Asp Ile Asp Ser Lys Val Thr Phe Ile Thr Gly Ser Val Ala Thr
        1060                1065                1070

Asp Glu Val Lys Pro Ala Leu Val Gly Val Gly Ser Trp Asn Gly Thr
1075                1080                1085                1090

Ser Tyr Thr Gln Asp Ala Ala Ala Thr Arg Leu Arg Ser Val Ala Asp
              1095                1100                1105

Phe Val Ala Glu Pro Val Ala Leu Gln Phe Ser Glu Gly Ile Asp Leu
              1110                1115                1120

Thr Asn Ala Thr Val Thr Val Thr Asn Ile Thr Asp Asp Lys Thr Val
          1125                1130                1135

Glu Val Ile Ser Lys Glu Ser Val Asp Ala Asp His Asp Ala Gly Ala
    1140                1145                1150

Thr Lys Glu Thr Leu Val Ile Asn Thr Val Thr Pro Leu Val Leu Asp
1155                1160                1165                1170

Asn Ser Lys Thr Tyr Lys Ile Val Val Ser Gly Val Lys Asp Ala Ala
              1175                1180                1185

Gly Asn Val Ala Asp Thr Ile Thr Phe Tyr Ile Lys
          1190                1195

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Primer T5-X

<400> SEQUENCE: 3
ttaatcgatt ctagatggat aggaaaaaag ctg                                33

<210> SEQ ID NO 4
<211> LENGTH: 37

```
<212> TYPE: DNA
<213> ORGANISM: Artificial Sequence
<220> FEATURE:
<223> OTHER INFORMATION: Description of Artificial Sequence: Primer E

<400> SEQUENCE: 4
atacccgggg gtacggatcc gatacagatt tgagcaa                              37

<210> SEQ ID NO 5
<211> LENGTH: 2763
<212> TYPE: DNA
<213> ORGANISM: Bacillus stearothermophilus
<220> FEATURE:
<221> NAME/KEY: CDS
<222> LOCATION: (1)..(2760)
<221> NAME/KEY: sig_peptide
<222> LOCATION: (1)..(93)
<221> NAME/KEY: mat_peptide
<222> LOCATION: (94)..(2760)

<400> SEQUENCE: 5
```

| | | | | | | | | | | | | | | | | |
|---|---|---|---|---|---|---|---|---|---|---|---|---|---|---|---|---|
| atg | gct | tat | caa | cct | aag | tcc | tat | cgc | aag | ttt | gtt | gcg | aca | act | gca | 48 |
| Met | Ala | Tyr | Gln | Pro | Lys | Ser | Tyr | Arg | Lys | Phe | Val | Ala | Thr | Thr | Ala | |
| | -30 | | | | -25 | | | | | -20 | | | | | | |
| aca | gct | gcc | atg | gta | gca | tct | gcg | gta | gct | cct | gta | gta | tct | gca | gca | 96 |
| Thr | Ala | Ala | Met | Val | Ala | Ser | Ala | Val | Ala | Pro | Val | Val | Ser | Ala | Ala | |
| -15 | | | | -10 | | | | | -5 | | | | | -1 | 1 | |
| agc | ttc | aca | gat | gtt | gcg | ccg | caa | tat | aaa | gat | gcg | atc | gat | ttc | tta | 144 |
| Ser | Phe | Thr | Asp | Val | Ala | Pro | Gln | Tyr | Lys | Asp | Ala | Ile | Asp | Phe | Leu | |
| | | | 5 | | | | | 10 | | | | | 15 | | | |
| gta | tca | act | ggt | gca | aca | aaa | ggt | aaa | aca | gaa | aca | aaa | ttc | ggc | gtt | 192 |
| Val | Ser | Thr | Gly | Ala | Thr | Lys | Gly | Lys | Thr | Glu | Thr | Lys | Phe | Gly | Val | |
| | | 20 | | | | | 25 | | | | | 30 | | | | |
| tac | gat | gaa | atc | act | cgt | cta | gat | gcg | gca | gtt | att | ctt | gca | aga | gta | 240 |
| Tyr | Asp | Glu | Ile | Thr | Arg | Leu | Asp | Ala | Ala | Val | Ile | Leu | Ala | Arg | Val | |
| | 35 | | | | | 40 | | | | | 45 | | | | | |
| tta | aaa | cta | gac | gtt | gac | aac | gca | aaa | gac | gca | ggc | ttc | aca | gat | gtg | 288 |
| Leu | Lys | Leu | Asp | Val | Asp | Asn | Ala | Lys | Asp | Ala | Gly | Phe | Thr | Asp | Val | |
| 50 | | | | | 55 | | | | | 60 | | | | | 65 | |
| cca | aaa | gac | cgt | gca | aaa | tac | gtc | aac | gcg | ctt | gta | gaa | gct | ggc | gta | 336 |
| Pro | Lys | Asp | Arg | Ala | Lys | Tyr | Val | Asn | Ala | Leu | Val | Glu | Ala | Gly | Val | |
| | | | 70 | | | | | 75 | | | | | 80 | | | |
| tta | aac | ggt | aaa | gca | cct | ggc | aaa | ttt | ggt | gca | tac | gac | cca | tta | act | 384 |
| Leu | Asn | Gly | Lys | Ala | Pro | Gly | Lys | Phe | Gly | Ala | Tyr | Asp | Pro | Leu | Thr | |
| | | | 85 | | | | | 90 | | | | | 95 | | | |
| cgc | gtt | gaa | atg | gca | aaa | atc | atc | gcg | aac | cgt | tac | aaa | tta | aaa | gct | 432 |
| Arg | Val | Glu | Met | Ala | Lys | Ile | Ile | Ala | Asn | Arg | Tyr | Lys | Leu | Lys | Ala | |
| | | | 100 | | | | | 105 | | | | | 110 | | | |
| gac | gat | gta | aaa | ctt | cca | ttc | act | gat | gta | aac | gat | aca | tgg | gca | cca | 480 |
| Asp | Asp | Val | Lys | Leu | Pro | Phe | Thr | Asp | Val | Asn | Asp | Thr | Trp | Ala | Pro | |
| | 115 | | | | | 120 | | | | | 125 | | | | | |
| tac | gta | aaa | gcg | ctt | tat | aaa | tac | gaa | gta | aca | aaa | ggt | aaa | aca | cca | 528 |
| Tyr | Val | Lys | Ala | Leu | Tyr | Lys | Tyr | Glu | Val | Thr | Lys | Gly | Lys | Thr | Pro | |
| 130 | | | | | 135 | | | | | 140 | | | | | 145 | |
| aca | agc | ttc | ggt | gca | tac | caa | aac | atc | act | cgc | ggt | gac | ttt | gcg | caa | 576 |
| Thr | Ser | Phe | Gly | Ala | Tyr | Gln | Asn | Ile | Thr | Arg | Gly | Asp | Phe | Ala | Gln | |
| | | | 150 | | | | | 155 | | | | | 160 | | | |
| ttt | gta | tat | aga | gcg | gtg | aat | att | aat | gca | gtg | cca | gaa | ata | gtt | gaa | 624 |
| Phe | Val | Tyr | Arg | Ala | Val | Asn | Ile | Asn | Ala | Val | Pro | Glu | Ile | Val | Glu | |
| | | | 165 | | | | | 170 | | | | | 175 | | | |
| gta | act | gcg | gtt | aat | tcg | act | aca | gtg | aaa | gta | aca | ttc | aat | acg | caa | 672 |
| Val | Thr | Ala | Val | Asn | Ser | Thr | Thr | Val | Lys | Val | Thr | Phe | Asn | Thr | Gln | |
| | 180 | | | | | 185 | | | | | 190 | | | | | |

```
att gct gat gtt gat ttc aca aat ttt gct atc gat aac ggt tta act       720
Ile Ala Asp Val Asp Phe Thr Asn Phe Ala Ile Asp Asn Gly Leu Thr
    195                 200                 205 gtt act aaa gca act ctt tct cgt gat aaa aaa tcc gta gag gtt gtg       768
Val Thr Lys Ala Thr Leu Ser Arg Asp Lys Lys Ser Val Glu Val Val
210                 215                 220                 225 gta aat aaa ccg ttt act cgt aat cag gaa tat aca att aca gcg aca       816
Val Asn Lys Pro Phe Thr Arg Asn Gln Glu Tyr Thr Ile Thr Ala Thr
                230                 235                 240 ggc att aaa aat tta aaa ggc gag acc gct aag gaa tta act ggt aag       864
Gly Ile Lys Asn Leu Lys Gly Glu Thr Ala Lys Glu Leu Thr Gly Lys
            245                 250                 255 ttt gtt tgg tct gtt caa gat gcg gta act gtt gca cta aat aat agt       912
Phe Val Trp Ser Val Gln Asp Ala Val Thr Val Ala Leu Asn Asn Ser
        260                 265                 270 tcg ctt aaa gtt gga gag gaa tct ggt tta act gta aaa gat cag gat       960
Ser Leu Lys Val Gly Glu Glu Ser Gly Leu Thr Val Lys Asp Gln Asp
    275                 280                 285 ggc aaa gat gtt gta ggt gct aaa gta gaa ctt act tct tct aat act      1008
Gly Lys Asp Val Val Gly Ala Lys Val Glu Leu Thr Ser Ser Asn Thr
290                 295                 300                 305 aat att gtt gta gtt tca agt ggc gaa gta tca gta tct gct gct aaa      1056
Asn Ile Val Val Ser Ser Gly Glu Val Ser Val Ser Ala Ala Lys
                310                 315                 320 gtt aca gct gta aaa ccg gga aca gct gat gtt act gca aaa gtt aca      1104
Val Thr Ala Val Lys Pro Gly Thr Ala Asp Val Thr Ala Lys Val Thr
            325                 330                 335 tta cca gat ggt gtt gta cta aca aat aca ttt aaa gtg aca gtt aca      1152
Leu Pro Asp Gly Val Val Leu Thr Asn Thr Phe Lys Val Thr Val Thr
        340                 345                 350 gaa gtg cct gtg caa gta caa aat caa gga ttt act tta gtt gat aat      1200
Glu Val Pro Val Gln Val Gln Asn Gln Gly Phe Thr Leu Val Asp Asn
    355                 360                 365 ctt tct aat gct cca cag aat aca gtt gca ttt aac aaa gct gag aaa      1248
Leu Ser Asn Ala Pro Gln Asn Thr Val Ala Phe Asn Lys Ala Glu Lys
370                 375                 380                 385 gta act tca atg ttt gct gga gaa act aaa aca gtt gca atg tat gat      1296
Val Thr Ser Met Phe Ala Gly Glu Thr Lys Thr Val Ala Met Tyr Asp
                390                 395                 400 act aaa aac ggt gat cct gaa act aaa cct gtt gat ttc aaa gat gca      1344
Thr Lys Asn Gly Asp Pro Glu Thr Lys Pro Val Asp Phe Lys Asp Ala
            405                 410                 415 act gta cgt tca tta aat cca att att gca aca gct gct att aat ggt      1392
Thr Val Arg Ser Leu Asn Pro Ile Ile Ala Thr Ala Ala Ile Asn Gly
        420                 425                 430 agt gag ctc ctt gtc aca gct aat gct ggc caa tct gga aaa gct tca      1440
Ser Glu Leu Leu Val Thr Ala Asn Ala Gly Gln Ser Gly Lys Ala Ser
    435                 440                 445 ttt gaa gta aca ttt aaa gat aat aca aaa aga aca ttt aca gtt gat      1488
Phe Glu Val Thr Phe Lys Asp Asn Thr Lys Arg Thr Phe Thr Val Asp
450                 455                 460                 465 gtg aaa aaa gac cct gta tta caa gat att aaa gta gat gca act tct      1536
Val Lys Lys Asp Pro Val Leu Gln Asp Ile Lys Val Asp Ala Thr Ser
                470                 475                 480 gtt aaa ctt tcc gat gaa gct gtt ggc ggc ggg gaa gtt gaa gga gtt      1584
Val Lys Leu Ser Asp Glu Ala Val Gly Gly Gly Glu Val Glu Gly Val
            485                 490                 495 aac caa aaa acg att aaa gta agt gca gtt gac caa tac ggt aaa gaa      1632
Asn Gln Lys Thr Ile Lys Val Ser Ala Val Asp Gln Tyr Gly Lys Glu
```

-continued

```
                500                     505                     510
att aaa ttt ggt aca aaa ggt aaa gtt act gtt aca act aat aca gaa    1680
Ile Lys Phe Gly Thr Lys Gly Lys Val Thr Val Thr Thr Asn Thr Glu
        515                     520                     525 gga cta gtt att aaa aat gta aat agc gat aat aca att gac ttt gat    1728
Gly Leu Val Ile Lys Asn Val Asn Ser Asp Asn Thr Ile Asp Phe Asp
530                     535                     540                 545 agc ggc aat agt gca act gac caa ttt gtt gtc gtt gca aca aaa gac    1776
Ser Gly Asn Ser Ala Thr Asp Gln Phe Val Val Val Ala Thr Lys Asp
                550                     555                     560 aaa att gtc aat ggt aaa gta gaa gtt aaa tat ttc aaa aat gct agt    1824
Lys Ile Val Asn Gly Lys Val Glu Val Lys Tyr Phe Lys Asn Ala Ser
        565                     570                     575 gac aca aca cca act tca act aaa aca att act gtt aat gta gtg aat    1872
Asp Thr Thr Pro Thr Ser Thr Lys Thr Ile Thr Val Asn Val Val Asn
            580                     585                     590 gta aaa gct gac gct aca cca gta gga tta gat att gta gca cct tct    1920
Val Lys Ala Asp Ala Thr Pro Val Gly Leu Asp Ile Val Ala Pro Ser
        595                     600                     605 gaa att gat gtg aat gct cca aac act gct tct act gca gat gtt gat    1968
Glu Ile Asp Val Asn Ala Pro Asn Thr Ala Ser Thr Ala Asp Val Asp
610                     615                     620                 625 ttt att aat ttc gaa agt gtt gag att tat aca ctc gat tct aat ggt    2016
Phe Ile Asn Phe Glu Ser Val Glu Ile Tyr Thr Leu Asp Ser Asn Gly
                630                     635                     640 aac cgt ctt aaa aaa gtt act cca act gca act aca ctt gta ggt act    2064
Asn Arg Leu Lys Lys Val Thr Pro Thr Ala Thr Thr Leu Val Gly Thr
        645                     650                     655 aat gat tat gtt gaa gtt aat ggg aat gta tta caa ttc aag ggt aac    2112
Asn Asp Tyr Val Glu Val Asn Gly Asn Val Leu Gln Phe Lys Gly Asn
            660                     665                     670 gat gaa tta acg cta tta act tct tct agt aca gta aac gtt gat gta    2160
Asp Glu Leu Thr Leu Leu Thr Ser Ser Ser Thr Val Asn Val Asp Val
        675                     680                     685 aca gct gat gga att aca aaa cgt att cca gta aaa tat atc aac tct    2208
Thr Ala Asp Gly Ile Thr Lys Arg Ile Pro Val Lys Tyr Ile Asn Ser
690                     695                     700                 705 gca agt gta cct gcc agt gca aca gta gca aca agt cct gtt act gtt    2256
Ala Ser Val Pro Ala Ser Ala Thr Val Ala Thr Ser Pro Val Thr Val
                710                     715                     720 aag ctt aat tca agt gat aat gat tta aca ttt gaa gaa tta ata ttc    2304
Lys Leu Asn Ser Ser Asp Asn Asp Leu Thr Phe Glu Glu Leu Ile Phe
        725                     730                     735 ggt gta att gac cct aca caa tta gtc aaa gat gaa gac atc aac gaa    2352
Gly Val Ile Asp Pro Thr Gln Leu Val Lys Asp Glu Asp Ile Asn Glu
            740                     745                     750 ttt att gca gtt tca aaa gcg gct aaa aat gat gga tat ttg tat aat    2400
Phe Ile Ala Val Ser Lys Ala Ala Lys Asn Asp Gly Tyr Leu Tyr Asn
        755                     760                     765 aaa ccg ctt gta acg gtt aaa gat gca tca gga aaa gtt att cca aca    2448
Lys Pro Leu Val Thr Val Lys Asp Ala Ser Gly Lys Val Ile Pro Thr
770                     775                     780                 785 ggt gca aat gtt tac ggt cta aat cat gat gca act aac gga aac att    2496
Gly Ala Asn Val Tyr Gly Leu Asn His Asp Ala Thr Asn Gly Asn Ile
                790                     795                     800 tgg ttt gat gag gaa caa gct ggc tta gct aaa aaa ttt agt gat gta    2544
Trp Phe Asp Glu Glu Gln Ala Gly Leu Ala Lys Lys Phe Ser Asp Val
        805                     810                     815 cat ttt gat gtt gat ttt tca tta gct aac gtt gta aaa act ggt agc    2592
```

```
His Phe Asp Val Asp Phe Ser Leu Ala Asn Val Val Lys Thr Gly Ser
        820                 825                 830 ggt aca gtt tct tca tcg cca tca tta tct gac gca att caa ctt act      2640
Gly Thr Val Ser Ser Ser Pro Ser Leu Ser Asp Ala Ile Gln Leu Thr
835                     840                 845 aat tca ggc gat gca gta tcg ttt aca tta gtt atc aaa tca att tat      2688
Asn Ser Gly Asp Ala Val Ser Phe Thr Leu Val Ile Lys Ser Ile Tyr
850                 855                 860                 865 gtt aaa ggc gca gat aaa gat gat aac tta ctt gca gcc cct gtt          2736
Val Lys Gly Ala Asp Lys Asp Asp Asn Asn Leu Leu Ala Ala Pro Val
            870                 875                 880 tct gtc aat gtg act gtg aca aaa taa                                  2763
Ser Val Asn Val Thr Val Thr Lys
            885

<210> SEQ ID NO 6
<211> LENGTH: 920
<212> TYPE: PRT
<213> ORGANISM: Bacillus stearothermophilus

<400> SEQUENCE: 6

Met Ala Tyr Gln Pro Lys Ser Tyr Arg Lys Phe Val Ala Thr Thr Ala
    -30                 -25                 -20

Thr Ala Ala Met Val Ala Ser Ala Val Ala Pro Val Val Ser Ala Ala
-15                 -10                  -5                  -1   1

Ser Phe Thr Asp Val Ala Pro Gln Tyr Lys Asp Ala Ile Asp Phe Leu
                 5                  10                  15

Val Ser Thr Gly Ala Thr Lys Gly Lys Thr Glu Thr Lys Phe Gly Val
            20                  25                  30

Tyr Asp Glu Ile Thr Arg Leu Asp Ala Val Ile Leu Ala Arg Val
    35                  40                  45

Leu Lys Leu Asp Val Asp Asn Ala Lys Asp Ala Gly Phe Thr Asp Val
50                  55                  60                  65

Pro Lys Asp Arg Ala Lys Tyr Val Asn Ala Leu Val Glu Ala Gly Val
                70                  75                  80

Leu Asn Gly Lys Ala Pro Gly Lys Phe Gly Ala Tyr Asp Pro Leu Thr
            85                  90                  95

Arg Val Glu Met Ala Lys Ile Ile Ala Asn Arg Tyr Lys Leu Lys Ala
            100                 105                 110

Asp Asp Val Lys Leu Pro Phe Thr Asp Val Asn Asp Thr Trp Ala Pro
115                 120                 125

Tyr Val Lys Ala Leu Tyr Lys Tyr Glu Val Thr Lys Gly Lys Thr Pro
130                 135                 140                 145

Thr Ser Phe Gly Ala Tyr Gln Asn Ile Thr Arg Gly Asp Phe Ala Gln
                150                 155                 160

Phe Val Tyr Arg Ala Val Asn Ile Asn Ala Val Pro Glu Ile Val Glu
            165                 170                 175

Val Thr Ala Val Asn Ser Thr Thr Val Lys Val Thr Phe Asn Thr Gln
            180                 185                 190

Ile Ala Asp Val Asp Phe Thr Asn Phe Ala Ile Asp Asn Gly Leu Thr
    195                 200                 205

Val Thr Lys Ala Thr Leu Ser Arg Asp Lys Ser Val Glu Val Val
210                 215                 220                 225

Val Asn Lys Pro Phe Thr Arg Asn Gln Glu Tyr Thr Ile Thr Ala Thr
            230                 235                 240

Gly Ile Lys Asn Leu Lys Gly Glu Thr Ala Lys Glu Leu Thr Gly Lys
```

-continued

```
                    245                 250                 255
Phe Val Trp Ser Val Gln Asp Ala Val Thr Val Ala Leu Asn Asn Ser
                260                 265                 270
Ser Leu Lys Val Gly Glu Glu Ser Gly Leu Thr Val Lys Asp Gln Asp
            275                 280                 285
Gly Lys Asp Val Val Gly Ala Lys Val Glu Leu Thr Ser Ser Asn Thr
290                 295                 300                 305
Asn Ile Val Val Ser Ser Gly Glu Val Ser Val Ser Ala Ala Lys
                310                 315                 320
Val Thr Ala Val Lys Pro Gly Thr Ala Asp Val Thr Ala Lys Val Thr
                325                 330                 335
Leu Pro Asp Gly Val Val Leu Thr Asn Thr Phe Lys Val Thr Val Thr
            340                 345                 350
Glu Val Pro Val Gln Val Gln Asn Gln Gly Phe Thr Leu Val Asp Asn
            355                 360                 365
Leu Ser Asn Ala Pro Gln Asn Thr Val Ala Phe Asn Lys Ala Glu Lys
370                 375                 380                 385
Val Thr Ser Met Phe Ala Gly Glu Thr Lys Thr Val Ala Met Tyr Asp
                390                 395                 400
Thr Lys Asn Gly Asp Pro Glu Thr Lys Pro Val Asp Phe Lys Asp Ala
            405                 410                 415
Thr Val Arg Ser Leu Asn Pro Ile Ile Ala Thr Ala Ile Asn Gly
            420                 425                 430
Ser Glu Leu Leu Val Thr Ala Asn Ala Gly Gln Ser Gly Lys Ala Ser
            435                 440                 445
Phe Glu Val Thr Phe Lys Asp Asn Thr Lys Arg Thr Phe Thr Val Asp
450                 455                 460                 465
Val Lys Lys Asp Pro Val Leu Gln Asp Ile Lys Val Asp Ala Thr Ser
                470                 475                 480
Val Lys Leu Ser Asp Glu Ala Val Gly Gly Glu Val Glu Gly Val
            485                 490                 495
Asn Gln Lys Thr Ile Lys Val Ser Ala Val Asp Gln Tyr Gly Lys Glu
            500                 505                 510
Ile Lys Phe Gly Thr Lys Gly Lys Val Thr Val Thr Thr Asn Thr Glu
            515                 520                 525
Gly Leu Val Ile Lys Asn Val Asn Ser Asp Asn Thr Ile Asp Phe Asp
530                 535                 540                 545
Ser Gly Asn Ser Ala Thr Asp Gln Phe Val Val Ala Thr Lys Asp
                550                 555                 560
Lys Ile Val Asn Gly Lys Val Glu Val Lys Tyr Phe Lys Asn Ala Ser
            565                 570                 575
Asp Thr Thr Pro Thr Ser Thr Lys Thr Ile Thr Val Asn Val Val Asn
            580                 585                 590
Val Lys Ala Asp Ala Thr Pro Val Gly Leu Asp Ile Val Ala Pro Ser
            595                 600                 605
Glu Ile Asp Val Asn Ala Pro Asn Thr Ala Thr Ala Asp Val Asp
610                 615                 620                 625
Phe Ile Asn Phe Glu Ser Val Glu Ile Tyr Thr Leu Asp Ser Asn Gly
                630                 635                 640
Asn Arg Leu Lys Lys Val Thr Pro Thr Ala Thr Thr Leu Val Gly Thr
            645                 650                 655
Asn Asp Tyr Val Glu Val Asn Gly Asn Val Leu Gln Phe Lys Gly Asn
            660                 665                 670
```

```
Asp Glu Leu Thr Leu Leu Thr Ser Ser Thr Val Asn Val Asp Val
    675                 680                 685

Thr Ala Asp Gly Ile Thr Lys Arg Ile Pro Val Lys Tyr Ile Asn Ser
690                 695                 700                 705

Ala Ser Val Pro Ala Ser Ala Thr Val Ala Thr Ser Pro Val Thr Val
                710                 715                 720

Lys Leu Asn Ser Ser Asp Asn Asp Leu Thr Phe Glu Leu Ile Phe
                725                 730                 735

Gly Val Ile Asp Pro Thr Gln Leu Val Lys Asp Glu Asp Ile Asn Glu
            740                 745                 750

Phe Ile Ala Val Ser Lys Ala Ala Lys Asn Asp Gly Tyr Leu Tyr Asn
    755                 760                 765

Lys Pro Leu Val Thr Val Lys Asp Ala Ser Gly Lys Val Ile Pro Thr
770                 775                 780                 785

Gly Ala Asn Val Tyr Gly Leu Asn His Asp Ala Thr Asn Gly Asn Ile
                790                 795                 800

Trp Phe Asp Glu Glu Gln Ala Gly Leu Ala Lys Lys Phe Ser Asp Val
            805                 810                 815

His Phe Asp Val Asp Phe Ser Leu Ala Asn Val Val Lys Thr Gly Ser
    820                 825                 830

Gly Thr Val Ser Ser Ser Pro Ser Leu Ser Asp Ala Ile Gln Leu Thr
835                 840                 845

Asn Ser Gly Asp Ala Val Ser Phe Thr Leu Val Ile Lys Ser Ile Tyr
850                 855                 860                 865

Val Lys Gly Ala Asp Lys Asp Asn Asn Leu Leu Ala Ala Pro Val
                870                 875                 880

Ser Val Asn Val Thr Val Thr Lys
                885

<210> SEQ ID NO 7
<211> LENGTH: 75
<212> TYPE: DNA
<213> ORGANISM: Artificial Sequence
<220> FEATURE:
<223> OTHER INFORMATION: Description of Artificial Sequence: signal
      sequence of the malE gen

<400> SEQUENCE: 7
atgaaaataa aaacaggtgc acgcatcctc gcattatccg cattaacgac gatgatgttt      60
tccgcctcgg ctctc                                                      75

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: signal
      sequence of gen3 of bacteriophage fd

<400> SEQUENCE: 8
gtgaaaaaat tattattcgc aattccttta gttgttcctt tctat                     45

<210> SEQ ID NO 9
<211> LENGTH: 49
<212> TYPE: DNA
<213> ORGANISM: Bacillus stearothermophilus

<400> SEQUENCE: 9
```

```
gaattcatcg atgtcgacca aggaggtcta gatggatccg gccaagctt         49
```

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: cloning
      strategy for pMAL-A

<400> SEQUENCE: 10

```
atcgagggaa ggatttcaga attcggatcc tctagagtcg acctgcaggc aagcttg    57
```

<210> SEQ ID NO 11
<211> LENGTH: 4988
<212> TYPE: DNA
<213> ORGANISM: Artificial Sequence
<220> FEATURE:
<223> OTHER INFORMATION: Description of Artificial Sequence: fusion of
      SbsA and MalE

<400> SEQUENCE: 11

```
atgaaaataa aaacaggtgc acgcatcctc gcattatccg cattaacgac gatgatgttt     60
tccgcctcgg ctctcgccaa aatcgaagaa ggtaaactgg taatctggat taacggcgat    120
aaaggctata acgtctcgc tgaagtcggt aagaaattca gaaagatac cggaattaaa     180 gtcaccgttg agcatccgga taactgaa gagaaattcc cacaggttgc ggcaactggc     240
gatggccctg acattatctt ctgggcacac gaccgctttg gtggctacgc tcaatctggc    300
ctgttggctg aaatcacccc ggacaaagcg ttccaggaca agctgtatcc gtttacctgg    360
gatgccgtac gttacaacgg caagctgatt gcttacccga tcgctgttga agcgttatcg    420
ctgatttata caaagatct gctgccgaac ccgccaaaaa cctgggaaga tcccggcg     480 ctggataaag aactgaaagc gaaagtaag agcgcgctga tgttcaacct gcaagaaccg    540
tacttcacct ggccgctgat tgctgctgac ggggttatg cgttcaagta tgaaaacggc    600
aagtacgaca ttaaagacgt gggcgtggat aacgctggcg cgaaagcggg tctgaccttc    660
ctggttgacc tgattaaaaa caaacacatg aatgcagaca ccgattactc catcgcagaa    720 gctgcctttta taaaggcga aacagcgatg accatcaacg gcccgtgggc atggtccaac    780
atcgacacca gcaaattgaa ttatggtgta acggtactgc cgaccttcaa gggtcaccca    840
tccaaaccgt tcgttggcgt gctgagcgca ggtattaacg ccgccagtcc gaacaaagag    900
ttggcgaaag agttcctcga aaactatctg ctgactgatg aaggtctgga agcggttaat    960
aaagacaaac gctgggtgc cgtagcgctg aagtcttacg aggaagagtt ggcgaaagat   1020
ccacgtattg ccgccaccat ggaaacgcc cagaaaggtg aaatcatgcc gaacatcccg   1080
cagatgtccg cttctggta tgccgtgcgt actgcggtga tcaacgccgc cagcggtcgt   1140
cagatcgtcg atgaagccct gaaagacgcg cagactaatt cgagctcgaa caacaacaac   1200
aataacaata caacaaccct cgggatcgag ggaaggattt cagaattcgg atccgctaca   1260
gatgtagcaa cagtagtaag ccaagcaaaa gcacagttca aaaagcata ctatacttac   1320 agccatacag taacggaaac tggtgaattc ccaaacatta cgatgtata tgctgaatac   1380 aacaaagcga aaaacgata ccgtgatgcg gtagcattag tgaataaagc aggtggcgcg   1440 aaaaagacg cttacttagc tgatttacaa aagaatatg aaacttacgt tttcaaagca   1500
aaccctaaat ctggcgaagc tcgtgtagca acttacatcg atgcttacaa ctatgcaaca   1560
aaattagacg aaatgcgcca agagctagag gctgctgttc aagcaaaaga tttagaaaaa   1620
```

```
gcagaacaat actatcacaa aattccttat gaaattaaaa ctcgcacagt cattttagat    1680
cgcgtatatg gtaaaacaac tcgtgattta cttcgctcta catttaaagc aaaagcacaa    1740
gaacttcgcg acagcttaat ttatgatatt accgttgcaa tgaaagcgcg cgaagtacaa    1800
gacgctgtga aagcaggcaa tttagacaaa gctaaagctg ctgttgatca atcaatcaa    1860 tacttaccaa aagtaacaga tgctttcaaa actgaactaa cagaagtagc gaaaaaagca    1920
ttagatgcag atgaagctgc gcttactcca aaagttgaaa gtgtaagtgc gattaacact    1980
caaaacaaag ctgttgaatt aacagcagta ccagtgaacg gaacactaaa attacaactt    2040
tcagctgctg caaatgaaga tacagtaaac gtaaatactg tacgtatcta taaagtggac    2100
ggtaacattc catttgccct taatacggca gatgtttctt tatctacaga cggaaaaact    2160
atcactgtgg atgcttcaac tccattcgaa aataatacgg agtataaagt agtagttaaa    2220
ggtattaaag acaaaaatgg caaagaattt aagaagatg cattcacttt caagcttcga    2280
aatgatgctg tagttactca agtgtttgga actaatgtaa caaacaacac ttctgtaaac    2340
ttagcagcag gtactttcga cactgacgat actttaacag tagtatttga taagttgtta    2400
gcacctgaaa ctgtaaacag ctcgaacgtt actattacag atgttgaaac tggaaaacgc    2460
attccagtaa ttgcatctac ttctggttct acaattacta ttacgttaaa agaagcgtta    2520
gtaactggta acaatataa acttgctatc aataatgtta aacattaac tggttacaat    2580 gcagaagctt acgagttagt gttcactgca acgcatcag caccaactgt tgctaccgct    2640
cctactactt taggtggtac aactttatct actggttctc ttacaacaaa tgtttggggt    2700
aaattggctg gtggtgtgaa tgaagctgga acttattatc ctggtcttca attcacaaca    2760
acgtttgcta ctaagttaga cgaatctact ttagctgata actttgtatt agttgaaaaa    2820
gaatctggta cagttgttgc ttctgaacta aaatataatg cagacgctaa atggtaact    2880 ttagtgccaa aagcggacct taaagaaaat acaatctatc aaatcaaaat taaaaaaggc    2940
ttgaagtccg ataaaggtat tgaattaggc actgttaacg agaaaacata tgagttcaaa    3000
actcaagact taactgctcc tacagttatt agcgtaacgt ctaaaaatgg cgacgctgga    3060
ttaaaagtaa ctgaagctca agaatttact gtgaagttct cagagaattt aaatacattt    3120
aatgctacaa ccgtttcggg tagcacaatc acatacggtc aagttgctgt agtaaaagcg    3180
ggtgcaaact tatctgctct tacagcaagt gacatcattc cagctagtgt tgaagcggtt    3240
actggtcaag atggaacata caaagtgaaa gttgctgcta accaattaga acgtaaccaa    3300
gggtacaaat tagtagtgtt cggtaaaggt gcaacagctc ctgttaaaga tgctgcaaat    3360
gcaaatactt tagcaactaa ctatatctat acatttacaa ctgaaggtca agacgtaaca    3420
gcaccaacgg ttacaaaagt attcaaaggt gattctttaa aagacgctga tgcagttact    3480
acacttacga acgttgatgc aggtcaaaaa ttcactatcc aatttagcga agaattaaaa    3540
acttctagtg gttctttagt gggtggcaaa gtaactgtcg agaaattaac aaacaacgga    3600
tgggtagatg ctggtactgg aacaactgta tcagttgctc ctaagacaga tgcaaatggt    3660
aaagtaacag ctgctgtggt tacattaact ggtcttgaca ataacgacaa agatgcgaaa    3720
ttgcgtctgg tagtagataa gtcttctact gatggaattg ctgatgtagc tggtaatgta    3780
attaaggaaa aagatatttt aattcgttac aacagctgga gacacactgt agcttctgtg    3840
aaagctgctg ctgacaaaga tggtcaaaac gcttctgctg cattcccaac aagcactgca    3900
attgatacaa ctaagagctt attagttgaa ttcaatgaaa ctgatttagc ggaagttaaa    3960
```

-continued

```
cctgagaaca tcgttgttaa agatgcagca ggtaatgcgg tagctggtac tgtaacagca    4020
ttagacggtt ctacaaataa atttgtattc actccatctc aagaattaaa agctggtaca    4080
gtttactctg taacaattga cggtgtgaga gataaagtag gtaacacaat ctctaaatac    4140
attacttcgt tcaagactgt atctgcgaat ccaacgttat cttcaatcag cattgctgac    4200
ggtgcagtta acgttgaccg ttctaaaaca attacaattg aattcagcga ttcagttcca    4260
aacccaacaa tcactcttaa gaaggctgac ggaacttcat ttactaatta cactttagta    4320
aatgtaaata atgaaaataa aacatacaaa attgtattcc acaaaggtgt aacacttgac    4380
gagtttactc aatatgagtt agcagtttca aaagattttc aaactggtac tgatattgat    4440
agcaaagtta cattcatcac aggttctgtt gctactgacg aagtaaaacc tgctctagta    4500
ggcgttggtt catggaatgg aacaagctat actcaggatg ctgcagcaac acgacttcgg    4560
tctgtagctg acttcgttgc ggagccagtt gcccttcaat tctcagaagg tatcgattta    4620
acgaatgcaa ctgtgacagt aacaaatatt actgatgata aaactgttga agttatttca    4680
aaagagagtg tagacgcaga ccatgatgca ggtgctacta aggagacatt agtaattaac    4740
acagttactc ctttagtact tgataacagc aagacttata agattgttgt aagtggagtt    4800
aaagatgcag caggtaatgt tgcagatact attacattct atattaagta atctgggcta    4860
ggtgtttgtc accgctcaag gttgtcaaaa tatgtcgaaa agctctgcgg agagaaatct    4920
ctgcggggct tttcttttg ctcaaatctg tatcaggatc ctctagagtc gacctgcagg    4980
caagcttg                                                             4988
```

<210> SEQ ID NO 12
<211> LENGTH: 3768
<212> TYPE: DNA
<213> ORGANISM: Artificial Sequence
<220> FEATURE:
<223> OTHER INFORMATION: Description of Artificial Sequence: fusion of
      SbsA with the signal sequenz of gen3 of bacteriophage fd

<400> SEQUENCE: 12

```
gtgaaaaaat tattattcgc aattccttta gttgttcctt tctatgcggc ccagccggcc      60
gctacagatg tagcaacagt agtaagccaa gcaaaagcac agttcaaaaa agcatactat     120
acttacagcc atacagtaac ggaaactggt gaattcccaa acattaacga tgtatatgct     180
gaatacaaca aagcgaaaaa acgataccgt gatgcggtag cattagtgaa taaagcaggt     240
ggcgcgaaaa aagacgctta cttagctgat ttacaaaaag aatatgaaac ttacgttttc     300
aaagcaaacc ctaaatctgg cgaagctcgt gtagcaactt acatcgatgc ttacaactat     360
gcaacaaaat tagacgaaat gcgccaagag ctagaggctg ctgttcaagc aaaagattta     420
gaaaaagcag aacaatacta tcacaaaatt ccttatgaaa ttaaaactcg cacagtcatt     480
ttagatcgcg tatatggtaa aacaactcgt gatttacttc gctctacatt taaagcaaaa     540
gcacaagaac ttcgcgacag cttaatttat gatattaccg ttgcaatgaa agcgcgcgaa     600
gtacaagacg ctgtgaaagc aggcaattta gacaaagcta agctgctgt tgatcaaatc     660 aatcaatact taccaaaagt aacagatgct ttcaaaactg aactaacaga agtagcgaaa     720
aaagcattag atgcagatga agctgcgctt actccaaaag ttgaaagtgt aagtgcgatt     780
aacactcaaa acaaagctgt tgaattaaca gcagtaccag tgaacggaac actaaaatta     840
caactttcag ctgctgcaaa tgaagataca gtaaacgtaa atactgtacg tatctataaa     900
gtggacggta acattccatt tgcccttaat acggcagatg tttctttatc tacagacgga     960
```

```
aaaactatca ctgtggatgc ttcaactcca ttcgaaaata atacgagta taaagtagta    1020
gttaaaggta ttaaagacaa aaatggcaaa gaatttaaag aagatgcatt cactttcaag    1080
cttcgaaatg atgctgtagt tactcaagtg tttggaacta atgtaacaaa caacacttct    1140
gtaaacttag cagcaggtac tttcgacact gacgatactt taacagtagt atttgataag    1200
ttgttagcac ctgaaactgt aaacagctcg aacgttacta ttacagatgt tgaaactgga    1260
aaacgcattc cagtaattgc atctacttct ggttctacaa ttactattac gttaaaagaa    1320
gcgttagtaa ctggtaaaca atataaactt gctatcaata atgttaaaac attaactggt    1380
tacaatgcag aagcttacga gttagtgttc actgcaaacg catcagcacc aactgttgct    1440
accgctccta ctactttagg tggtacaact ttatctactg gttctcttac aacaaatgtt    1500
tggggtaaat tggctggtgg tgtgaatgaa gctggaactt attatcctgg tcttcaattc    1560
acaacaacgt ttgctactaa gttagacgaa tctactttag ctgataactt tgtattagtt    1620
gaaaaagaat ctggtacagt tgttgcttct gaactaaaat ataatgcaga cgctaaaatg    1680
gtaactttag tgccaaaagc ggaccttaaa gaaaatacaa tctatcaaat caaaattaaa    1740
aaaggcttga agtccgataa aggtattgaa ttaggcactg ttaacgagaa aacatatgag    1800
ttcaaaactc aagacttaac tgctcctaca gttattagcg taacgtctaa aaatggcgac    1860
gctggattaa aagtaactga agctcaagaa tttactgtga agttctcaga gaatttaaat    1920
acatttaatg ctacaaccgt ttcgggtagc acaatcacat acggtcaagt tgctgtagta    1980
aaagcgggtg caaacttatc tgctcttaca gcaagtgaca tcattccagc tagtgttgaa    2040
gcggttactg gtcaagatgg aacatacaaa gtgaaagttg ctgctaacca attagaacgt    2100
aaccaagggt acaaattagt agtgttcggt aaaggtgcaa cagctcctgt taaagatgct    2160
gcaaatgcaa atactttagc aactaactat atctatacat ttacaactga aggtcaagac    2220
gtaacagcac caacggttac aaaagtattc aaaggtgatt cttttaaaga cgctgatgca    2280
gttactacac ttcgaacgt tgatgcaggt caaaaattca ctatccaatt tagcgaagaa    2340
ttaaaaactt ctagtggttc tttagtgggt ggcaaagtaa ctgtcgagaa attaacaaac    2400
aacggatggg tagatgctgg tactggaaca actgtatcag ttgctcctaa gacagatgca    2460
aatggtaaag taacagctgc tgtggttaca ttaactggtc ttgacaataa cgacaaagat    2520
gcgaaattgc gtctggtagt agataagtct tctactgatg gaattgctga tgtagctggt    2580
aatgtaatta aggaaaaaga tattttaatt cgttacaaca gctggagaca cactgtagct    2640
tctgtgaaag ctgctgctga caaagatggt caaaacgctt ctgctgcatt cccaacaagc    2700
actgcaattg atacaactaa gagcttatta gttgaattca atgaaactga tttagcggaa    2760
gttaaacctg agaacatcgt tgttaaagat gcagcaggta atgcggtagc tggtactgta    2820
acagcattag acggttctac aaataaattt gtattcactc catctcaaga attaaaagct    2880
ggtacagttt actctgtaac aattgacggt gtgagagata aagtaggtaa cacaatctct    2940
aaatacatta cttcgttcaa gactgtatct gcgaatccaa cgttatcttc aatcagcatt    3000
gctgacggtg cagttaacgt tgaccgttct aaaacaatta caattgaatt cagcgattca    3060
gttccaaacc caacaatcac tcttaagaag gctgacggaa cttcatttac taattacact    3120
ttagtaaatg taaataatga aaataaaaca tacaaaattg tattccacaa aggtgtaaca    3180
cttgacgagt ttactcaata tgagttagca gtttcaaaag atttcaaac tggtactgat    3240
attgatagca aagttacatt catcacaggt tctgttgcta ctgacgaagt aaaacctgct    3300
ctagtaggcg ttggttcatg gaatggaaca agctatactc aggatgctgc agcaacacga    3360
```

```
cttcggtctg tagctgactt cgttgcggag ccagttgccc ttcaattctc agaaggtatc    3420
gatttaacga atgcaactgt gacagtaaca aatattactg atgataaaac tgttgaagtt    3480
atttcaaaag agagtgtaga cgcagaccat gatgcaggtg ctactaagga gacattagta    3540
attaacacag ttactccttt agtacttgat aacagcaaga cttataagat tgttgtaagt    3600
ggagttaaag atgcagcagg taatgttgca gatactatta cattctatat taagtaatct    3660
gggctaggtg tttgtcaccg ctcaaggttg tcaaaatatg tcgaaaagct ctgcggagag    3720
aaatctctgc gggcttttc ttttgctca aatctgtatc gcggccgc                   3768
```

<210> SEQ ID NO 13
<211> LENGTH: 4065
<212> TYPE: DNA
<213> ORGANISM: Artificial Sequence
<220> FEATURE:
<223> OTHER INFORMATION: Description of Artificial Sequence: fusion of
      SbsB with MalE

<400> SEQUENCE: 13

```
atgaaaataa aacaggtgc acgcatcctc gcattatccg cattaacgac gatgatgttt     60
tccgcctcgg ctctcgccaa atcgaagaa ggtaaactgg taatctggat taacggcgat    120
aaaggctata acgtctcgc tgaagtcggt aagaaattcg agaaagatac cggaattaaa    180
gtcaccgttg agcatccgga taactgaa gagaaattcc cacaggttgc ggcaactggc    240
gatggccctg acattatctt ctgggcacac gaccgctttg gtggctacgc tcaatctggc    300
ctgttggctg aaatcacccc ggacaaagcg ttccaggaca gctgtatcc gtttacctgg    360 gatgccgtac gttacaacgg caagctgatt gcttacccga tcgctgttga agcgttatcg    420
ctgatttata caaagatct gctgccgaac ccgccaaaaa cctgggaaga tcccggcg     480 ctggataaag aactgaaagc gaaagtaag agcgcgctga tgttcaacct gcaagaaccg    540
tacttcacct ggccgctgat tgctgctgac ggggttatg cgttcaagta tgaaaacggc    600
aagtacgaca ttaagacgt gggcgtggat aacgctggcg cgaaagcggg tctgaccttc    660
ctggttgacc tgattaaaaa caaacacatg aatgcagaca ccgattactc catcgcagaa    720 gctgcctta ataaggcga acagcgatg accatcaacg gcccgtgggc atggtccaac    780
atcgacacca gcaaattgaa ttatggtgta acggtactgc cgaccttcaa gggtcacca    840 tccaaaccgt tcgttggcgt gctgagcgca ggtattaacg ccgccagtcc gaacaaagag    900
ttggcgaaag agttcctcga aaactatctg ctgactgatg aaggtctgga agcggttaat    960
aaagacaaac cgctgggtgc cgtagcgctg aagtcttacg aggaagagtt ggcgaaagat   1020
ccacgtattg ccgccaccat ggaaacgcc cagaaaggtg aaatcatgcc gaacatcccg   1080
cagatgtccg ctttctggta tgccgtgcgt actgcggtga tcaacgccgc cagcggtcgt   1140
cagatcgtcg atgaagccct gaaagacgcg cagactaatt cgagctcgaa caacaacaac   1200
aataacaata caacaaccct cgggatcgag ggaaggattt cagaattcgg atccgcaagc   1260
ttcacagatg ttgcgccgca atataaagat gcgatcgatt tcttagtatc aactggtgca   1320 acaaaggta aacagaaac aaaattcggc gtttacgatg aaatcactcg tctagatgcg   1380
gcagttattc ttgcaagagt attaaaacta gacgttgaca acgcaaaaga cgcaggcttc   1440
acagatgtgc caaagaccg tgcaaaatac gtcaacgcgc ttgtagaagc tggcgtatta   1500
aacggtaaag cacctggcaa atttggtgca tacgaccat taactcgcgt tgaaatggca   1560
aaaatcatcg cgaaccgtta caattaaaa gctgacgatg taaaacttcc attcactgat   1620
```

-continued

```
gtaaacgata catgggcacc atacgtaaaa gcgctttata aatacgaagt aacaaaaggt    1680
aaaacaccaa caagcttcgg tgcataccaa aacatcactc gcggtgactt tgcgcaattt    1740
gtatatagag cggtgaatat taatgcagtg ccagaaatag ttgaagtaac tgcggttaat    1800
tcgactacag tgaaagtaac attcaatacg caaattgctg atgttgattt cacaaatttt    1860
gctatcgata acgtttaac tgttactaaa gcaactcttt ctcgtgataa aaaatccgta     1920
gaggttgtgg taaataaacc gtttactcgt aatcaggaat atacaattac agcgacaggc    1980
attaaaaatt taaaggcga gaccgctaag gaattaactg gtaagtttgt ttggtctgtt     2040
caagatgcgg taactgttgc actaaataat agttcgctta agttggaga ggaatctggt     2100 ttaactgtaa aagatcagga tggcaaagat gttgtaggtg ctaaagtaga acttacttct    2160
tctaatacta atattgttgt agtttcaagt ggcgaagtat cagtatctgc tgctaaagtt    2220
acagctgtaa aaccgggaac agctgatgtt actgcaaaag ttacattacc agatggtgtt    2280
gtactaacaa atacatttaa agtgacagtt acagaagtgc ctgtgcaagt acaaaatcaa    2340
ggatttactt tagttgataa tcttctaat gctccacaga atacagttgc atttaacaaa    2400
gctgagaaag taacttcaat gtttgctgga gaaactaaaa cagttgcaat gtatgatact    2460
aaaaacggtg atcctgaaac taaacctgtt gatttcaaag atgcaactgt acgttcatta    2520
aatccaatta ttgcaacagc tgctattaat ggtagtgagc tccttgtcac agctaatgct    2580
ggccaatctg gaaaagcttc atttgaagta acatttaaag ataatacaaa agaacatttt    2640
acagttgatg tgaaaaaaga ccctgtatta caagatatta agtagatgc aacttctgtt     2700 aaactttccg atgaagctgt tggcggcggg gaagttgaag gagttaacca aaaaacgatt    2760
aaagtaagtg cagttgacca atacggtaaa gaaattaaat ttggtacaaa aggtaaagtt    2820
actgttacaa ctaatacaga aggactagtt attaaaaatg taaatagcga taatacaatt    2880
gactttgata gcggcaatag tgcaactgac caatttgttg tcgttgcaac aaaagacaaa    2940
attgtcaatg gtaaagtaga agttaaatat ttcaaaaatg ctagtgacac aacaccaact    3000
tcaactaaaa caattactgt taatgtagtg aatgtaaaag ctgacgctac accagtagga    3060
ttagatattg tagcaccttc tgaaattgat gtgaatgctc caaacactgc ttctactgca    3120
gatgttgatt ttattaattt cgaaagtgtt gagatttata cactcgattc taatggtaac    3180
cgtcttaaaa aagttactcc aactgcaact acacttgtag gtactaatga ttatgttgaa    3240
gttaatggga atgtattaca attcaagggt aacgatgaat taacgctatt aacttcttct    3300
agtacagtaa acgttgatgt aacagctgat ggaattacaa aacgtattcc agtaaaaatat   3360 atcaactctg caagtgtacc tgccagtgca acagtagcaa caagtcctgt tactgttaag    3420
cttaattcaa gtgataatga tttaacattt gaagaattaa tattcggtgt aattgaccct    3480
acacaattag tcaaagatga agacatcaac gaatttattg cagtttcaaa agcggctaaa    3540
aatgatggat atttgtataa taaaccgctt gtaacggtta aagatgcatc aggaaaagtt    3600
attccaacag gtgcaaatgt ttacggtcta aatcatgatg caactaacgg aaacatttgg    3660
tttgatgagg aacaagctgg cttagctaaa aaatttagtg atgtacattt tgatgttgat    3720
ttttcattag ctaacgttgt aaaaactggt agcggtacag tttcttcatc gccatcatta    3780
tctgacgcaa ttcaacttac taattcaggc gatgcagtat cgtttacatt agttatcaaa    3840
tcaatttatg ttaaaggcgc agataaagat gataataact tacttgcagc ccctgttttct   3900 gtcaatgtga ctgtgacaaa ataattttga ggttcggtct ctgttaccat ttgaaaaatg    3960
```

-continued

```
ccgaaaagct ctgcggagag aaatctctgc ggggcttttc tttttggttc tatgtcaatt    4020
gttgaggtgc atggatcctc tagagtcgac ctgcaggcaa gcttg                    4065
```